United States Patent [19]

Albrecht et al.

[11] Patent Number: 5,755,671
[45] Date of Patent: May 26, 1998

[54] METHOD AND APPARATUS FOR ASSESSING CARDIOVASCULAR RISK

[75] Inventors: Paul Albrecht, Bedford, Mass.; J. Thomas Bigger, New Rochelle, N.Y.; Richard J. Cohen, Waban, Mass.

[73] Assignee: Massachusetts Institute of Technology, Cambridge, Mass.

[21] Appl. No.: 539,402

[22] Filed: Oct. 5, 1995

[51] Int. Cl.⁶ ............................................. A61B 5/0468
[52] U.S. Cl. ........................................................ 600/516
[58] Field of Search ........................... 128/696, 698, 128/702, 703–705, 706, 920, 923–925; 364/413.05, 413.06; 600/509, 511, 515–518, 521

[56] References Cited

U.S. PATENT DOCUMENTS

| | | | |
|---|---|---|---|
| 4,832,038 | 5/1989 | Arai et al. | 128/702 X |
| 5,265,617 | 11/1993 | Verrier et al. | 128/704 |
| 5,277,190 | 1/1994 | Moulton | 128/705 |
| 5,291,400 | 3/1994 | Gilham | 128/702 |
| 5,419,338 | 5/1995 | Sarma et al. | 128/703 |
| 5,427,285 | 6/1995 | Verrier et al. | 128/702 |
| 5,560,370 | 10/1996 | Verrier et al. | 128/705 |

*Primary Examiner*—Jeffrey R. Jastrzab
*Attorney, Agent, or Firm*—Choate, Hall & Stewart

[57] ABSTRACT

The method for assessing risk of an adverse clinical event includes detecting a physiologic signal in the subject and determining from the physiologic signal a sequence of intervals corresponding to time intervals between heart beats. The long-time structure of fluctuations in the intervals over a time period of more than fifteen minutes is analyzed to assess risk of an adverse clinical event. In a preferred embodiment, the physiologic signal is an electrocardiogram and the time period is at least fifteen minutes. A preferred method for analyzing the long-time structure variability in the intervals includes computing the power spectrum and fitting the power spectrum to a power law dependence on frequency over a selected frequency range such as $10^{-4}$ to $10^{-2}$ Hz. Characteristics of the long-time structure fluctuations in the intervals is used to assess risk of an adverse clinical event.

56 Claims, 6 Drawing Sheets

METHOD AND APPARATUS FOR ASSESSING CARDIOVASCULAR RISK

The Government has rights in this invention pursuant to National Institutes of Health (NIH) grant HL-39291 from the National Heart, Lung, and Blood Institute, Bethesda, Md. and by NASA Grant NAGW-3927.

BACKGROUND OF THE INVENTION

This invention relates to methods and apparatus for assessing risk of an adverse clinical event. An adverse clinical event includes, but is not limited to, adverse cardiovascular events such as occurrence of serious heart rhythm disturbances such as ventricular tachycardia and ventricular fibrillation, myocardial infarction, sudden cardiac death, myocardial infarction, development of heart failure, stroke, etc; an adverse clinical event may include as well other adverse events such as death from any cause, loss of consciousness, development of diminished cerebral function, development of a condition requiring hospitalization, etc.

The interbeat interval of the heart fluctuates in time. The variability in the interbeat interval can arise from a number of different physiologic mechanisms. One primary mechanism normally involved in generating the variability in the interbeat interval is the modulation of the activity of the sino-atrial node by the autonomic nervous system. The autonomic nervous system can alter the firing rate of the sino-atrial node, which functions as the heart's normal pacemaker responsible for the initiation of the heartbeat. In addition, variation in interbeat interval can be caused by circulating catecholamines which modulate the firing rate of the sino-atrial node. Variation in interbeat interval can also relate to variation in the time required for the electrical impulse to conduct through the heart's conduction system. Also, heart beats which originate at abnormal sites in the heart (i.e., not the sino-atrial node) generally are associated with substantial variation in the interbeat intervals that end or begin with those beats. Such abnormal, or ectopic, beats can often be recognized in that they are frequently associated with electrocardiographic waveforms of abnormal shape. In practice a normal beat may be identified by determining whether the shape of the associated electrocardiographic waveform is within normal limits and whether the interbeat intervals ending and beginning with that beat are within normal limits. The interval between two normal beats is termed an NN interval.

Since much of the variability in the interbeat interval in normally conducted heart beats is associated with the ongoing modulation of the sino-atrial node by the autonomic nervous system, analysis of variability in interbeat intervals (or equivalently, analysis of variability in heart rate which is proportional to the reciprocal of the interbeat interval) has been used to assess autonomic nervous system function. In the remainder of this document reference to variability in interbeat interval should be construed to include variability in any quantity, such as heart rate, which may be derived from the interbeat intervals. The sequence of interbeat intervals may be conveniently obtained from analysis of physiologic signals such as the electrocardiogram or the arterial blood pressure using techniques well known in the art. For example, the interbeat intervals may be measured by measuring the intervals between R waves (RR intervals) in the electrocardiogram signal. Furthermore, the RR intervals of the electrocardiogram can be easily and accurately measured from portable recording devices which monitor the electrocardiogram over periods of many hours, or even one or more days, in ambulatory subjects. Thus analysis of interbeat interval variability is a convenient and readily available noninvasive approach to assessing autonomic nervous system function.

Interbeat interval variability has been analyzed in a number of different ways. One class of techniques which has been used to analyze variability in the interval between heart beats involves time domain analysis. In this approach, one analyzes the variability in the interbeat intervals over time, or equivalently over beat number. Examples of time domain measurements include the measurement the standard deviation or variance of the interbeat intervals over a time period, the distribution density function of interbeat interval magnitudes (the proportions of intervals falling within sequential incremental ranges of interbeat interval) over a time period, and the serial autocorrelation coefficients of the interbeat intervals over a time period.

Another class of techniques that have been used to analyze interbeat interval variability involves frequency domain analysis. In the this class of techniques the variability in the interbeat intervals is represented in the frequency domain, often using Fourier transform methods. One example of frequency domain analysis involves computation of the power spectrum (often termed the power spectral density) of fluctuations in interbeat interval, or other signals which may be derived from the interbeat interval sequence. Power spectra computed from short data segments, approximately 5 minutes in length, of interbeat interval data generally provide information on the frequency content of the interbeat intervals above approximately 0.01 Hertz. Such power spectra, see FIG. 10a, are found to often have a peak at the frequency of respiration which generally falls in the 0.15 to 0.40 Hertz range of frequencies. This peak, termed the high frequency (HF) peak, has been found to reflect activity of the parasympathetic limb of the autonomic nervous system. An additional peak, termed the low frequency (LF) peak is often found in the 0.04 to 0.15 Hertz band. This peak has been found to reflect activity of the sympathetic limb of the autonomic nervous system as well as the parasympathetic limb. The ratio of the areas within these two frequency bands (LF/HF ratio), representing the ratio of the energies of the fluctuations within these two frequency bands, has been used as a measure of the balance between sympathetic and parasympathetic activity.

In addition to computation of the power spectrum over short periods of time, longer term recording of interbeat interval data have been analyzed using frequency domain techniques. For example, the power spectrum analysis of 24 hour recordings of interbeat interval data have been performed. Such analyses, see for example FIG. 10b, reveal that, at frequencies below approximately 0.02 Hertz down to approximately $10^{-5}$ Hertz, the relationship between the logarithm of the power spectrum amplitude and the logarithm of the frequency is described by a straight line. This, as shown below, is equivalent to the relationship given by the following equation:

$$P = Cf^\alpha,$$

where P is the power spectral density, C is a proportionality constant, f is frequency and $\alpha$ is a negative exponent. This relationship is termed a power law dependence of spectral power on frequency. Taking the logarithm of the above equation, one obtains:

$$\log(P) = \log(C) + \alpha \log(f),$$

where log denotes the logarithm function. This demonstrates that the linear relationship between the logarithm of the power spectrum and the logarithm of frequency is equivalent to a power law relationship between the magnitude of the power spectrum and frequency. The slope of the linear relationship is in fact equal to the exponent α. This dependence of the power spectrum on frequency at frequencies below approximately 0.02 Hertz, was not previously known to be associated with the risk of future adverse clinical events.

A variety of techniques have been used to analyze variability in interbeat interval to assess risk of an adverse clinical event. For example, some of these techniques involve obtaining measures of the distribution of the magnitudes of the interbeat intervals such as the standard deviation of the NN intervals (SDNN), the integral of the distribution density function of NN intervals divided by the maximum of the distribution density function (HRV Triangular Index), baseline width of a triangular approximation to the distribution density function (TINN—triangular interpolation of NN interval histogram). Other techniques which involve segmentation of the data include the measurement of the difference between the average of the NN intervals at night and the average of the NN intervals during the day (Night-Day Difference), the mean of the standard deviations of the NN intervals within 5-minute segments (SDNN Index), the standard deviation of the average of the NN intervals within 5-minute segments—each average being weighted by the fraction of the 5 minutes that has normal RR intervals—(SDANN Index). Other techniques involve measurements related to the relationship between the lengths of adjacent normal interbeat intervals. Such measures include the number, proportion or percent of adjacent normal RR intervals whose lengths differ by more than fifty milliseconds (NN50, pNN50 or pNN50% respectively), and the root mean square successive difference of normal RR intervals (rMSSD). Other techniques involve computation of the energy in various frequency bands of the power spectrum of interbeat intervals (see Berger R. D., Akselrod S., Gordon, and Cohen R. J. "An Efficient Algorithm for Spectral Analysis of Heart Rate Variability", IEEE Transactions on Biomedical Engineering, 33:900–904, 1986). Measures obtained with such techniques include the energy in the power spectrum up to 0.40 Hz (Total Power), energy in the power spectrum up to 0.0033 Hz (ULF—Ultra Low Frequency—Power), energy in the power spectrum between 0.0033 and 0.04 Hz (Very Low frequency—VLF—Power), energy in the power spectrum between 0.04 and 0.15 Hz (Low Frequency—LF—Power), energy in the power spectrum between 0.15 Hz and 0.40 Hz (High Frequency—HF—Power), ratio of LF and HF power (LF/HF Ratio). The LF/HF ratio was computed because it was thought to be a measure of sympathetic/parasympathetic balance, not as a means to measure the structure of the power spectrum.

Alterations in autonomic tone are thought to be associated with physiologic states associated with altered cardiac state. For example, patients with heart failure are known to have diminished parasympathetic nervous system activity (one component of the autonomic nervous system), and enhanced levels of sympathetic nervous system activity (another component of the autonomic nervous system). Both have been shown to enhance susceptibility to life threatening heart rhythm disturbances. Previous measures derived from analyses of interbeat interval variability have shown some relationship to the subsequent occurrence of adverse clinical events. These measures, however, do not predict an individual's risk of an adverse clinical event with sufficient accuracy to justify therapeutic intervention. Since the sequence of interbeat intervals may be easily and noninvasively obtained even in ambulatory subjects, what is needed is a more effective means of analyzing interbeat interval variability to accurately assess an individual's risk of an adverse clinical event.

SUMMARY OF THE INVENTION

This invention relates to method and apparatus for assessing risk of an adverse clinical event by analysis of variability in intervals between heart beats in terms of the long-time structure of fluctuations of the interbeat intervals.

The method of the invention, in one aspect, includes detecting a physiologic signal in a subject and determining from the physiologic signal a sequence of intervals corresponding to time intervals between heart beats. Long-time structure of variability in the intervals over a time period of more than fifteen minutes is analyzed to assess risk of an adverse clinical event. In a preferred embodiment, the physiologic signal is an electrocardiogram and the time period is at least one hour. This embodiment includes computing the power spectrum and the amplitude of the power spectrum at a specified frequency is estimated. A suitable specified frequency is approximately $10^{-4}$ Hz. The method of the invention may also include fitting the power spectrum to a power law dependence on frequency over a selected frequency range such as approximately $10^{-4}$ to $10^{-2}$ Hz. The amplitude of the power law dependence is determined at a specified frequency.

In yet another embodiment of the invention the method further includes fitting the logarithm of the power spectrum to a linear dependence on the logarithm of frequency over a selected frequency range such as approximately $10^{-4}$ to $10^{-2}$ Hz. In this embodiment, the amplitude of the linear dependence is determined at a specified frequency. In this embodiment, the risk of an adverse clinical event is determined by comparing the amplitude of the power spectrum with a predetermined risk-related cutpoint amplitude. Risk may also be assessed by comparing the amplitude of the power law dependence with a predetermined risk-related cutpoint amplitude. Further, the exponent characterizing the power law dependence is compared with a predetermined risk-related cutpoint exponent to assess risk.

In another aspect, the invention includes determining a frequency within the selected frequency range at which amplitude of the linear dependence has a low correlation with the slope of the linear dependence when applied to a reference population.

In yet another aspect of the invention the method for assessing risk of an adverse clinical event includes detecting an electrocardiogram signal in a subject and determining from the electrocardiogram a sequence of intervals corresponding to time intervals between heartbeats. The power spectrum of the sequence of intervals over a time period of more than six hours is computed and the logarithm of the power spectrum is fitted to a linear dependence on the logarithm of frequency over the frequency range of approximately $10^{-4}$ to $10^{-2}$ Hz. Risk of an adverse clinical event is based on one or more characteristics of the linear dependence. Suitable characteristics include slope of the linear dependence and amplitude of the linear dependence at a specified frequency.

In one preferred embodiment, long-time structure of fluctuations in interbeat intervals is characterized by computing the serial autocorrelation coefficients of the interbeat intervals; in another preferred embodiment the interbeat intervals are converted to a time-based signal and the autocorrelation function of the signal is computed. The long-time structure is then analyzed by examining the dependence of the autocorrelation coefficients on delay-number, or autocorrelation function on delay-time, at delays corresponding to approximately one minute or longer. In another preferred embodiment, the power spectrum of the fluctuations in interbeat interval is computed and the dependence of the power spectrum on frequency at frequencies below approximately 0.02 Hertz is analyzed. The power spectrum may be estimated by many techniques well known in the art such as Fourier transform methods, autoregressive moving average methods, and the like. In another preferred embodiment, complex demodulation is used to define the long-time structure of the fluctuations in the frequency domain.

In other preferred embodiments, many other techniques known in the art are used to analyze the long-time structure of fluctuations in interbeat interval either in the time domain, frequency domain, or other domains. For example, in one preferred embodiment the variability of interbeat interval is analyzed utilizing segments of at least two different lengths. One aspect of this embodiment involves analyzing variability within segments. Another aspect involves analyzing the variability between segments of a measure of the intervals within segments. In one example of this embodiment, the interbeat interval sequence is first divided up into segments of length a, then divided into segments of length b and then into segments of length c and so on. One then computes the average standard deviation or variance of NN intervals within segments of each length (for example, SDNN-a Index, SDNN-b Index, SDNN-c Index, etc). Analysis of the dependence, for example, of the SDNN Index, on segment length provides information on the long-time structure of the fluctuations. In another aspect of this embodiment, one computes, for different segment lengths, the standard deviation of the average of the NN intervals in each segment (i.e. SDANN-a Index, SDANN-b Index, SDANN-c Index). The dependence of the SDANN Index on segment length provides information on the long-time structure of the fluctuations.

In another preferred embodiment, the energy of the fluctuations in two or more frequency bands, at least one including a region below 0.02 Hertz, are computed (for example by computing and integrating the power spectrum over these bands, or by band-pass filtering a signal related to the interbeat intervals). The dependence of energy on frequency band is analyzed to characterize the long-time structure of the fluctuations and thereby to assess risk of an adverse clinical event. For example, the ratio or difference of energy in the two frequency bands is computed to obtain a measure of risk of an adverse clinical event. In another preferred embodiment, the power of the fluctuations at two or more frequencies, at least one of which is below 0.02 Hertz, are computed (for example by computing and measuring the amplitude of the power spectrum at these frequencies, or by notch filtering a signal related to the interbeat intervals). The dependence of power on frequency is analyzed to characterize the long-time structure of the fluctuations and thereby to assess risk of an adverse clinical event. For example, the ratio or difference of power at the two frequencies is computed to obtain a measure of risk of an adverse clinical event.

It is understood that the method of this invention includes all techniques that may be used to analyze the long-time structure of fluctuations in interbeat interval in order to assess risk of an adverse clinical event (for example, methods involving computation of autoregression coefficients, complex demodulation, transform methods, wavelet expansions and the like).

DESCRIPTION OF THE PREFERRED EMBODIMENT

Figure 1:
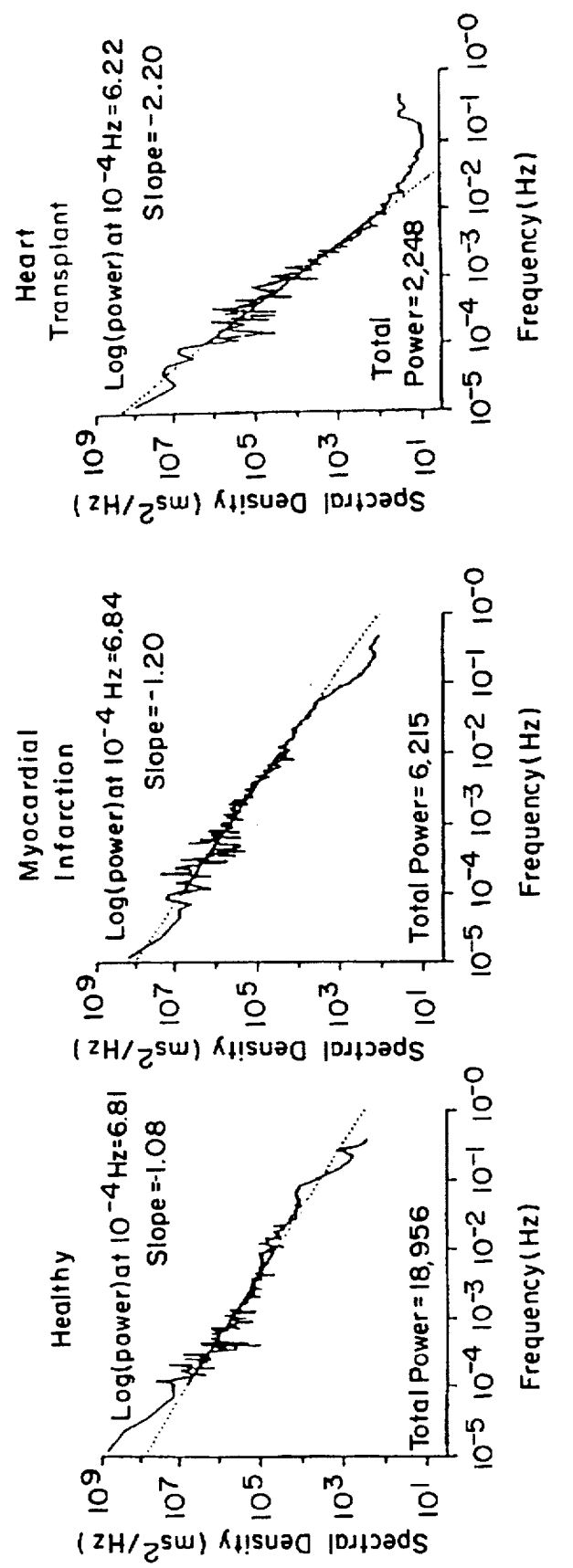
FIGS. 1($a$), 1($b$) and 1($c$) are log—log graphs of 24-hour RR power spectra. The computer power law regression lines are superimposed on the data; the solid portions of the lines are the segments between $10^{-4}$ and $10^{-2}$ Hz. The left panel shows data from a healthy subject, the middle panel shows data from a patient 11 days after myocardial infarction, and the right panel shows data from a heart transplant patient (denervated heart). For each example, total power ($ms^2$) was near the median for the group.

This invention relates to the assessment of risk of an adverse clinical event by analysis of the long-time structure of fluctuations in interbeat interval. The inventors discovered that the power law dependence of the power spectrum on frequency at frequencies below approximately 0.02 Hertz, which is remarkable in that the relationship is consistent over at least three decades of frequency, provides extremely accurate information on the risk of an adverse clinical event. In particular the risk of a future adverse clinical event increases strongly as the logarithm of the power law relationship at a given frequency decreases and the slope becomes more negative. For example, in a group of 715 patients after myocardial infarction, as shown in the Example below—see FIG. 5, 21 patients determined to be at 'high risk', because each had a highly negative slope and decreased log(power) at $10^{-4}$ Hertz, had a three year mortality of 83%, whereas 470 patients determined to be at 'low risk', because each had a less negative slope and higher log(power) at $10^{-4}$ Hertz, had a three year mortality of only 11%. Thus the 21 patients found to be at 'high risk' according to the method of this invention had approximately a 7.5 times greater risk of mortality compared to the 470 patients found to be at 'low risk' according to the method of this invention.

The power law dependence of the power spectrum on frequency expresses a relationship indicating a consistent increase in the power of fluctuations in interbeat interval as frequency decreases at frequencies below approximately 0.02 Hertz. This invention involves the discovery that the shape of the power spectrum, i.e. the dependence of the power spectrum on frequency, at frequencies below approximately 0.02 Hertz is directly related to the risk of an adverse clinical event such as mortality. The power spectrum represents one frequency domain technique for measuring the properties of fluctuations in interbeat interval at frequencies below approximately 0.02 Hertz. The power spectrum may be computed according to a wide variety of techniques such as methods involving the use of Fourier transforms, autoregressive techniques and other methods known in the art. Other frequency domain methods that could be equivalently used to measure the properties of fluctuations in interbeat interval at frequencies below approximately 0.02 Hertz include, for example, sine or cosine transform methods, or complex demodulation.

The properties of fluctuations in interbeat interval at frequencies below 0.02 Hertz relate to the behavior of the fluctuations over long periods of time. Long periods of time refer in this document refer to time periods on the order of one minute or longer, corresponding to frequencies less than approximately 0.02 Hertz. Thus properties of fluctuations in interbeat interval at frequencies below approximately 0.02 Hertz, such as the power law dependence of the power spectrum on frequency, relate to the long-time structure of the fluctuations in interbeat interval. To examine the long-time structure of the fluctuations one generally requires a sequence of interbeat intervals corresponding to a data record of a length which is a large multiple of one minute—generally at least 15 minutes.

This invention relates to methods and apparatus for assessing risk of an adverse clinical event by analysis of the long-time structure of fluctuations in interbeat interval. The analysis of the long-time structure may be performed in the frequency domain as described above, in the time domain (for example by autocorrelation analysis), or using other means for representing the fluctuations (for example, using polynomial expansion, wavelet representation, Laplace or other transform methods, etc.). All these methods can provide information on the structure of long-time fluctuations in interbeat interval. This structure refers to the shape of the fluctuations, for example the waveform of a fluctuation as it evolves over a period of time. In the frequency domain, the structure of a fluctuation reflects the dependence on frequency of the Fourier transform of the waveform of the fluctuation.

Previously used techniques used to analyze interbeat interval variability to assess risk of adverse clinical events described above in the Background of the Invention, do not characterize structure of fluctuations in interbeat interval over long periods of time (long-time structure). These techniques do not analyze information related to the sequence in time of the fluctuations in the intervals—except perhaps over short periods of time or by measuring the energy of fluctuations in a frequency band or by measuring night-day differences in an average measure—and thus do not constitute methods for assessing long-time structure of the variability in interbeat intervals as hereby defined in this document. Some of the previous techniques discussed above characterize the distribution of magnitudes of interbeat intervals (such as SDNN, total power), measure the energy of fluctuations in a frequency band (such as ULF or VLF power) or over particular time periods (such as SDNN Index or SDANN Index), but do not specifically characterize the structure of the fluctuations as they evolve over time. The LF/HF ratio is a measure of the short time-structure of the fluctuations in interbeat interval but not long-time structure. To analyze the structure of interbeat interval fluctuations one must analyze the shape of the in the time domain, in the frequency domain or in other domains reflecting other representations of the fluctuations. Structure analysis generally involves a minimum of two measures of the fluctuation in the time, frequency or other domains. The long-time structure refers to the evolution of the fluctuations for times scales approximately on the order of a minute or longer. In the frequency domain, this corresponds to frequencies less than roughly 0.02 Hertz.

This invention relates to the analysis of the long-time structure of the variability in interbeat interval to assess risk of an adverse clinical event. This invention is based on the discovery that information related to the risk of future adverse clinical events is contained in the long-time structure of fluctuations in interbeat interval.

According to the method of this invention long-time structure of the fluctuations in interbeat interval is analyzed to assess risk of an adverse clinical event. In one preferred embodiment, long-time structure in interbeat interval is characterized by computing the serial autocorrelation coefficients of the interbeat intervals; in another preferred embodiment the interbeat intervals are converted to a time-based signal and the autocorrelation function of the signal is computed. The long-time structure is then analyzed by examining the dependence of the autocorrelation coefficients on delay-number, or autocorrelation function on delay-time, including delays corresponding to approximately one minute or longer. In another preferred embodiment, the power spectrum of the fluctuations in interbeat interval is computed and the dependence of the power spectrum on frequency at frequencies below approximately 0.02 Hertz is analyzed. The power spectrum may be estimated by many techniques well known in the art such as Fourier transform methods, autoregressive methods, and the like. In another preferred embodiment, complex demodulation is used to define the long-time structure of the fluctuations in the frequency domain.

In other preferred embodiments, many other techniques known in the art are used to analyze the long-time structure of fluctuations in interbeat interval either in the time domain, frequency domain, or other domains. For example, in one preferred embodiment the variability of interbeat interval is analyzed utilizing segments of at least two different lengths. One aspect of this embodiment involves analyzing variability within segments. Another aspect involves analyzing the variability between segments of a measure of the intervals within segments. In one example of this embodiment, the interbeat interval sequence is first divided up into segments of length a, then divided into segments of length b and then into segments of length c and so on. One then computes the average standard deviation or variance of NN intervals within segments of each length (for example, SDNN-a Index, SDNN-b Index, SDNN-c Index, etc). Analysis of the dependence, for example, of the SDNN Index, on segment length provides information on the long-time structure of the fluctuations. In another aspect of this embodiment, one computes, for different segment lengths, the standard deviation of the average of the NN intervals in each segment (i.e. SDANN-a Index, SDANN-b Index, SDANN-c Index). The dependence of the SDANN Index on segment length provides information on the long-time structure of the fluctuations.

In another preferred embodiment, the energy of the fluctuations in two or more frequency bands, at least one including a region below 0.02 Hertz, are computed (for example by computing and integrating the power spectrum over these bands, or by band-pass filtering a signal related to the interbeat intervals). The dependence of energy on frequency band is analyzed to characterize the long-time structure of the fluctuations and thereby to assess clinical risk. For example, the ratio or difference of energy in the two frequency bands is computed to obtain a measure of risk of an adverse clinical event. In another preferred embodiment, the power of the fluctuations at two or more frequencies, at least one of which is below 0.02 Hertz, are computed (for example by computing and measuring the amplitude of the power spectrum at these frequencies, or by notch filtering a signal related to the interbeat intervals). The dependence of power on frequency is analyzed to characterize the long-time structure of the fluctuations and thereby to assess clinical risk. For example, the ratio or difference of power at the two frequencies is computed to obtain a measure of risk of an adverse clinical event.

According to the method of the invention the recording of the physiologic signal from the subject may be performed while the patient is resting, ambulating freely, or engaged in an activity protocol.

It is understood that the method of this invention includes all techniques that may be used to analyze the long-time structure of fluctuations in interbeat interval in order to assess risk of an adverse clinical event (for example, methods involving computation of autoregression coefficients, complex demodulation, transform methods, wavelet expansions and the like) Below we present one preferred embodiment of the invention which illustrates the great power of the invention for assessing risk of an adverse clinical event from the analysis of interbeat interval variability.

The following portion of the Description of the Preferred Embodiment up to the discussion of the apparatus implementing the present invention constitutes the verbatim text, figures and tables from a manuscript entitled "Power Law Behavior of RR Interval Variability in Healthy Middle-Aged Persons, Patients with Recent Acute Myocardial Infarction, and Patients with Heart Transplants" by J. Thomas Bigger, Jr., Richard C. Steinman, Linda M. Rolnitzky, Joseph L. Fleiss, Paul Albrecht, and Richard J. Cohen submitted for publication.

The theories and experiments on which the present invention is based will now be discussed. In 1982, Kobayashi and Musha reported the frequency dependence of the power spectrum of RR interval fluctuations in a normal young man. Kobayoshi, M. et al., "1/f Fluctuation of Heartbeat Period," *IEEE Trans. Biomed. Eng. BME*, 29:456–457, 1982. They computed the power spectrum of a 10-hour recording of RR intervals made in a laboratory setting and plotted the resulting power and frequency on a log—log graph. Over a frequency range from 0.0001 Hz to 0.02 Hz, they found that the plot was described by a straight line with a slope approximately equal to −1, indicating that the power decreased approximately as the reciprocal of frequency, 1/f. In 1988, Saul et al. performed power spectral analyses of 24-hour ambulatory ECG recordings from five healthy young men and found that over about four decades of frequency (0.00003 to almost 0.1 Hz) that the power spectrum's dependence on frequency is described by a power law $$P=Cf^\alpha \tag{1}$$

where P is the power spectral density, f is frequency, $\alpha$ is a negative exponent, and C is a proportionality constant, Saul, J. P. et al, "Analysis of Long Term Heart Rate Variability: Methods, 1/f Scaling and Implications," *Computers in Cardiology, IEEE Computer Society Press*, 14:419–422 (1987); $\alpha$ also corresponds to the slope of the log P versus log f relationship $$\log P = \log C + \alpha \log F \tag{2}$$

With spectral power and frequency both plotted on log scales, the slope of the relationship was about −1; Saul et al. found that $\alpha$ averaged −1.02±0.05 and ranged from −0.93 to −1.07 in healthy young men.

Experiments were designed and carried out by the inventors herein (1) to establish normal values for the regression of spectral power on frequency for RR interval fluctuations in healthy middle-aged persons; (2) to determine the effects of myocardial infarction on the regression of log(power) on log(frequency); (3) to determine the effect of cardiac denervation on the regression of log(power) on log(frequency); and (4) to assess the ability of power law regression parameters to predict death after myocardial infarction.

Patient groups

We studied three groups: (1) a group with recent myocardial infarction; (2) a group of healthy middle-aged persons matched on age and sex to the infarct sample; and (3) a group of patients with heart transplants. The patients with myocardial infarction were participants in the Multicenter Post Infarction Program (MPIP), a prospective natural history study of myocardial infarction. The Multicenter Post Infarction Research Group, "Risk Stratification and Survival After Myocardial Infarction," *N Eng. J. Med.* 309:331–336, 1983; Bigger, J. T. et al, "The Relationships Among Ventricular Arrhythmias, Left Ventricular Dysfunction and Mortality in the 2 Years After Myocardial Infarction," *Circulation* 69:250–258, 1984. The MPIP sample of patients was selected to be representative of the entire myocardial infarction population. The details concerning enrollment, measurement of baseline variables, quality control procedures and follow-up have been described previously. The 24-hour electrocardiographic recordings were made 11±3 days after acute myocardial infarction. The sample of healthy persons was recruited to match the myocardial infarction sample for age and sex. Bigger, J. T. et al, "RR Variability in Healthy, Middle-Aged Persons Compared with Patients with Chronic Coronary Heart Disease of Recent Acute Myocardial Infarction," *Circulation* 91:1936–1943, 1995. The group of patients with heart transplants were participants in a study of psychoactive responsiveness (6). They were 47±11 years of age and were studied between 3 and 4 months after their heart transplant. Transplant patients were excluded for hypertension (blood pressure>160/100), heart failure, or transplant rejection. 24-Hour ECG recordings were made with patients off all adrenergic agonist or antagonist medication or psychoactive drugs, but all were taking cyclosporin and prednisone.

Study design

To determine the effects of acute myocardial infarction on the regression of log(power) on log(frequency) of RR fluctuations, we compared the healthy group with the patients with recent myocardial infarction. To determine the effect of cardiac denervation on the regression of log(power) on log(frequency) of RR fluctuations, we compared the healthy sample with the heart transplant patients.

Processing of 24-Hour Holter Recordings

We processed 24-hour Holter tape or cassette recordings using recently described methods. Briefly, the 24-hour recordings were digitized by a Marquette 8000 scanner and submitted to the standard Marquette algorithms for QRS labeling and editing (version 5.8 software). Then, the data files were transferred via high speed link from the Marquette scanner to a Sun 4/75 workstation where a second stage of editing was done, using algorithms developed at Columbia University, to find and correct any remaining errors in QRS labeling that could adversely affect measurement of RR variability. Bigger et al., "Components of Heart Rate Variability Measured During Healing of Acute Myocardial Infarction," *Am. J. Cardiol.* 61:208–215, 1988. Long and short RR intervals in all classes, normal to normal, normal to atrial premature complex, normal to ventricular premature complex, were reviewed iteratively until all errors were corrected. For a tape to be eligible for this study, we required it to have $\geq 12$ hours of analyzable data and have at least half of the nighttime (00:00–05:00) and daytime (07:30–21:30) periods analyzable. At least 50% of each period had to be sinus rhythm. Bigger et al., "Correlations Among Time and Frequency Domain Measures of Heart Period Variability Two Weeks After Myocardial Infarction," *Am. J. Cardiol.* 69:891–898, 1992. The average duration of the ECG recordings was $\geq 23$ hours for the three samples and $\geq 99\%$ of all RR intervals were consecutive normal complexes.

Time Series Analysis of Normal RR Intervals

Frequency Domain Analysis. After the second stage of editing and review of the results by a cardiologist, the RR interval power spectrum was computed over the entire recording interval (usually 24 hours) using a method first described by Albrecht and Cohen, "Estimation of Heart Rate Power Spectrum Bands from Real-World Data: Dealing With Ectopic Beats and Noisy Data," *Computers in Cardiology* 15:311–314, 1988. Our adaptation of the method was described by Rottman et al., "Efficient Estimation of the Heart Period Power Spectrum Suitable for Physiology or Pharmacologic Studies," *Am. J. Cardiol.* 66:1522–1524, 1990. First, a regularly spaced time series was derived from the RR intervals by sampling the irregularly spaced series defined by the succession of normal RR intervals. For each Holter ECG recording, $2^{18}$ points were sampled; for recordings precisely 24-hours in duration, the sampling interval was 329 ms. A "boxcar" low-pass filter with a window twice the sampling interval was then applied. Gaps in the time series resulting from noise or ectopic beats were filled in with linear splines which can cause a small reduction in high frequency power but does not affect other components of the power spectrum.

A fast Fourier transform was computed and the resulting 24-hour RR interval power spectrum was corrected for the attenuating effects of both the filtering and the sampling (see Albrecht and Cohen, above). Frequency domain measures of RR variability were computed by integrating the point power spectrum over their frequency intervals as previously described. Bigger et al., "Frequency Domain Measures of Heart Period Variability and Mortality After Myocardial Infarction," *Circulation* 85:164–171, 1992. We calculated the power within four frequency bands of the 24-hour RR interval power spectrum: (1) <0.0033 Hz, ultra low frequency power (ULF), (2) 0.0033 to <0.04 Hz, very low frequency power (VLF), (3) 0.04 to <0.15 Hz, low frequency power (LF), and (4) 0.15 to <0.40 Hz, high frequency power (HF). In addition, we calculated total power (power in the band <0.40 Hz) and the ratio of low to high frequency (LF/HF) power, a measure that has been used as an indicator of sympatho-vagal balance. Pagani et al., "Power Spectral Analysis of Heart Rate and Arterial Pressure Variabilities as a Marker of Sympatho-Vagal Interaction in Man and Conscious Dog," Circ. Res. 59:178–193, 1986. High values for the ratio suggest predominance of sympathetic nervous activity.

Regression and correlation analyses. For each Holter recording, the regression of log(power) on log(frequency) was computed using previously described techniques (see, Saul, above). Briefly, the point power spectrum described above was logarithmically smoothed in the frequency domain by first calculating the common log of frequency and then integrating power into bins spaced 60 per decade, i.e., 0.0167 log(Hz) wide. Because each successive decade has 10 times the number of points as the previous decade, bins at higher frequency contain more points than those at lower frequencies. A regression analysis of log(power) on log(frequency) was performed on the linear portion of the smoothed power spectrum—between $10^{-4}$ and $10^{-2}$ Hz—and the slope and intercept at 10–4 Hz derived. We chose this frequency because it is the furthest from the non-linear portion of the smoothed power spectrum, the LF and HF power bands.

Individual regression equations were derived for each of the 274 healthy subjects, for the 715 patients with recent myocardial infarction, and for the 19 patients with heart transplants. Then, an "average" regression equation was obtained for each of these three groups. For each group, this average regression line had, as its slope and $10^{-4}$ Hz intercept, the average of the slopes and intercepts of the individual regression lines. 95% confidence bands were calculated for each group. Each confidence band was the average of the 95% confidence bands for all subjects in a group. These group confidence bands were calculated by averaging the values of each individual lower and upper 95% confidence band over the range of x-values between $10^{-4}$ Hz and $10^{-2}$ Hz.

For the group with recent myocardial infarction, we wanted an intercept that would be statistically independent of slope and would thus represent an upper limit of predictive accuracy to predict mortality. Among the resulting 715 regression equations in this group, preliminary examination of the correlation between the slope and values of the function at different points on the abscissa revealed that for selected higher values, e.g. –2 (i.e., $10^{-2}$ Hz), the power and slope had a positive correlation and that for selected lower values, e.g. –4 (i.e., $10^{-4}$ Hz), a negative correlation. These observations implied the existence of at least one point on the abscissa where the correlation between log(power) and slope would be zero. In order to obtain independent measures for statistical analyses, we established a procedure to evaluate the correlation between slope and log(power) as a function of frequency and locate the "zero-correlation" point. We call the intercept at this point the "zero-correlation log(power)."

Statistical Procedures

Survival Analytic Methods. We calculated Kaplan-Meier survival functions, see Kaplan et al., "Nonparametric Estimation from Incomplete Observations, "J. Am. Stat. Assoc. 53:457–481, 1958, to display graphically the survival experience of the MPIP sample of patients over a 3-year interval of time and to tabulate survival rates up to a prespecified time, 3 years. We performed Cox proportional hazards analyses, see Cox, "Regression Models and Life Tables, " (with discussion) J. R. Stat. Soc. B. 34:187–220, 1972, when testing hypotheses about the association between one or more risk predictors and mortality. The Cox regression model allowed us to adjust for covariates. The P2L BMDP computer program was used to carry out the Cox survival analyses. Dixon et al., "BMDP Statistical Software," Los Angeles: University of California Press, 719–743, 1988. This program permits categorical and continuous predictor variables to be analyzed together. The Cox proportional hazards model provides a measure of association, the hazard ratio, that is not linked to a single time point. Cox model survival analysis estimates the independent effects of each of several predictor variables on survival. The hazard function, i.e., the instantaneous probability of dying at any point in time, is assumed in the Cox model to be proportional to the exponential functions $exp(\Sigma B_i X_i)$ where the $B_i$'s are the regression coefficients and the $X_i$'s are the values of the predictor variables. The values of the regression coefficients are assumed to remain constant over time, and each $exp(B_i)$ is interpretable as a relative risk for variable i: $exp(B_i)$ is the ratio of instantaneous probabilities of dying for patients with values of $X_i$ 1 unit apart, holding all other variables constant.

Dichotomizing Predictor Variables. To find the best cut-point to dichotomize slope, log(power) at $10^{-4}$ Hz, and zero-correlation log(power), we sought the dichotomization cutpoint that maximized the hazard ratio obtained from the Cox regression models with all-cause mortality as the endpoint. Given the need for adequate numbers of patients in each subgroup when testing hypotheses, we restricted our search to dichotomizations from the 10th to 65th percentiles. We calculated the hazard ratio for each possible dichotomization cutpoint within this interval (unadjusted for any covariates), and identified the point at which the hazard ratio attained its maximum value. In addition to Cox analyses where all-cause mortality was the endpoint, these dichotomization cutpoints were used in Cox analyses using cardiac mortality and arrhythmic mortality as the endpoints. Hinckle et al., "Clinical Classification of Cardiac Deaths," Circulation 65:457–464, 1982.

Association Between Power Spectral Regression Parameters and Mortality

We used the Cox proportional hazards survival model to determine whether the slope, the log power) at $10^{-4}$ Hz, or the zero-correlation log(power) predicted all-cause mortality, cardiac mortality or arrhythmic mortality when used alone or when adjusted for five important post infarction risk predictors that we previously found strongly associated with mortality. Slope and the two power measures were dichotomized so that the relative strengths of association could be estimated. For these analyses, the additional covariates were coded to provide the best fitting model to predict mortality. Bigger, J. T. et al., "The Relationships Among Ventricular Arrhythmias, Left Ventricular Dysfunction and Mortality in the 2 Years After Myocardial Infarction," Circulation 69:250–258, 1984; Bigger et al., "Correlations Among Time and Frequency Domain Measures of Heart Period Variability Two Weeks After Myocardial Infarction," Am. J. Cardiol. 69:891–898, 1992. Age was divided into three categories <50, 50–59, $\geq 60$. New York Heart Association functional class was dichotomized at Class I or II versus III or IV. Rales were dichotomized at none or basilar versus greater than basilar. Left ventricular ejection fraction was coded on a 4-interval scale in accordance with the relation between ejection fraction and mortality: <0.20, 0.20–0.29, 0.30–0.39, and ≧0.40. The average frequency of ventricular premature complexes was also coded on a 4-interval scale: none, ≧0 but <3 per hour, ≧3 but <10 per hour, and ≧10 per hour.

Similar sets of analyses (i.e., variable alone and then adjusted for five post infarction risk predictors—read above—with all-cause mortality, cardiac mortality, or arrhythmic mortality as endpoints) were performed for the slope, the log(power) at $10^{-4}$ Hz, and the zero-correlation log(power) as well as for the following power spectral measures: ULF power (dichotomized at 1600 ms$^2$), VLF power (dichotomized at 180 ms$^2$), LF power (dichotomized at 35 ms$^2$), HF power (dichotomized at 20 ms$^2$), total power (dichotomized at 2000 ms$^2$). These frequency measures were analyzed in order to compare their predictive power with that of the slope and of the two measures of spectral power. All variables were dichotomized to provide ease of interpretation.

The above sequence of analyses (i.e., variable(s) alone and then adjusted for the above five risk predictors, using the three mortality endpoints) were performed using the following variables simultaneously: (1) the slope and the log (power) at $10^{-4}$ Hz and (2) the slope and the zero-correlation log(power). This was done to assess the independent predictive power of both variables together, unadjusted and adjusted for the above five risk predictors.

To determine if power law spectral analysis would improve positive predictive accuracy for all-cause mortality, we combined slope and log(power) at $10^{-4}$ Hz into a "joint variable." Using the dichotomization cutpoints for each variable as described above, patients were categorized as high risk by this "joint variable" if they were so categorized by both slope and log(power) at $10^{-4}$ Hz. This enabled us to compare subjects at high risk by slope and log(power) at $10^{-4}$ with all other subjects. We did this also for slope and zero-correlation log(power).

Jackknife Method. We used the jackknife technique to obtain an unbiased standard error of the mean (SEM) for the difference between two correlated relative risks. Miller, "The Jackknife—A Review," *Biometrika* 61:1–15, 1974. One relative risk was obtained when both the slope and the log(power) at $10^{-4}$ Hz were used as the components of a joint predictor of mortality. The second relative risk was obtained when the slope and the zero-correlation log(power) were used together. These joint predictors were dichotomized; they were set to 1 if both variables were in the high-risk range, and to 0 otherwise. There was a correlation between the log(power) at $10^{-4}$ Hz in one joint predictor and the zero-correlation log(power) in the second joint predictor, resulting in an association between the two joint predictors. In our analyses, the statistic jackknifed was the difference between the two relative risks. A SEM was derived. The difference between jackknifed relative risks, divided by the SEM, was referred for significance to a table of critical values of the normal distribution.

Results

Power Law Parameters of the 24-Hour RR Interval Time Series for Healthy Persons Compared with Those for the Myocardial Infarction Group and with Those for the Heart Transplant Group (Denervated Hearts)

FIGS. 1(a)–(c) show 24-hour RR interval power spectra for a typical individual from each of the three groups we studied. In each example, the individual selected for display had total power near the median for the group he/she represented. The RR interval power spectra demonstrate the inverse power law relation between power and frequency, indicated by a downward sloping straight line from $10^{-4}$ to $10^{-2}$ Hz on the log—log graph. The slope of the regression of log(power) on log(frequency) is somewhat steeper for the myocardial infarction patient and much steeper for the transplant patient (denervated heart) when compared with the healthy subject. Compared with the area under the entire 24-hour RR interval power spectrum for the healthy subject, the area for the patient with recent myocardial infarction is about one-third and the area for the patient with a heart transplant is about one-tenth.

Figure 2:
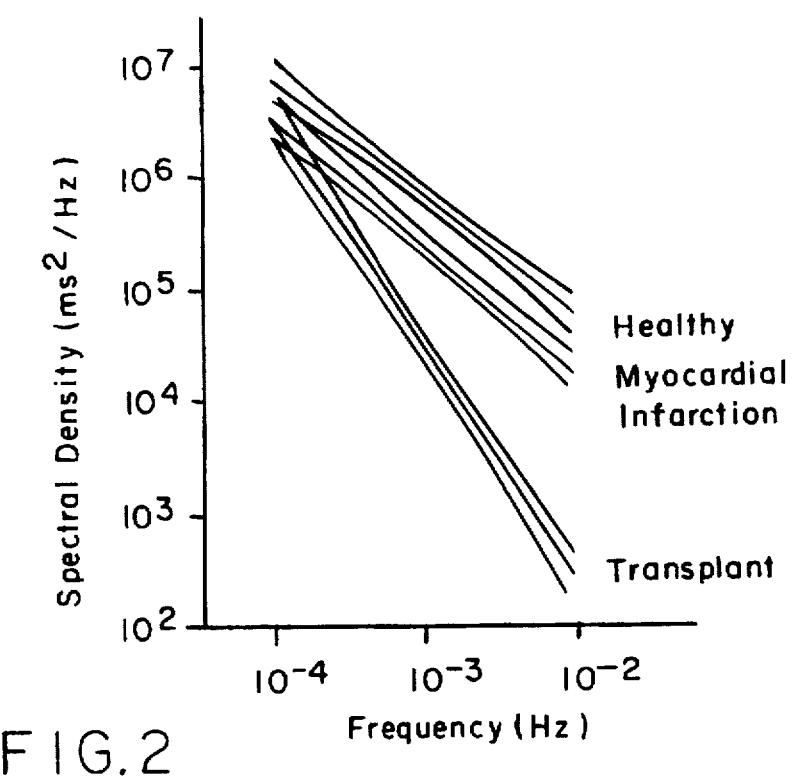
FIG. 2 is a graph of regression of log(power) on log (frequency) for healthy subjects (n=274), myocardial infarction patients (n=715), and heart transplant patients (n-19). Each regression line is the average of the regression lines for all subjects in a group. Each confidence band is the average of the 95% confidence bands for all subjects in a group. For the healthy group, power drops approximately one log unit for each log unit increase in frequency. For the heart transplant group, power drops approximately two log units for each log unit increase in frequency. The average slope for the myocardial infarction group has a value between the healthy group and the heart transplant group. The changes in slope in the myocardial infarction group and the heart transplant group indicate relatively greater loss of power at higher frequencies compared to the healthy group.

FIG. 2 compares the average regression lines for the three groups. The regression lines for the myocardial infarction and transplant groups are shifted downward and are steeper relative to the healthy group; both changes are significant. The average slope of log(power) on log(frequency) indicates that the decrease in power at higher frequency values is much greater for the heart transplant group than for the healthy group. These data are presented numerically in Table 1.

TABLE 1

Power Spectral Measures of RR Variability for Healthy Middle-Aged Subjects (n = 274), Patients with Recent Myocardial Infarction (n = 715), and Heart Transplant Patients (n = 19)

| Power Measure | Healthy | Post-Infarction | Transplant |
| --- | --- | --- | --- |
| Slope* | −1.06 ± 0.12 | −1.15 ± 0.19 | −2.08 ± 0.22 |
| Log(power) at $10^{-4}$ Hz† | 6.87 ± 0.24 | 6.56 ± 0.36 | 6.56 ± 0.29 |
| Power, ms$^2$ | | | |
| Total | 21,222 ± 11,663 | 7,623 ± 6,049 | 3,716 ± 3,410 |
| Ln(Total) | 9.83 ± 0.51 | 8.65 ± 0.80 | 7.95 ± 0.70 |
| ULF | 18,420 ± 10,639 | 6,280 ± 5,089 | 3,678 ± 3,357 |
| Ln(ULF) | 9.68 ± 0.54 | 8.45 ± 0.80 | 7.94 ± 0.70 |
| VLF | 1,782 ± 965 | 899 ± 855 | 14 ± 28 |
| Ln(VLF) | 7.35 ± 0.53 | 6.36 ± 1.03 | 2.09 ± 0.94 |
| LF | 790 ± 563 | 303 ± 373 | 7 ± 15 |
| Ln(LF) | 6.45 ± 0.68 | 5.08 ± 1.22 | 1.03 ± 1.22 |
| HF | 228 ± 282 | 139 ± 213 | 15 ± 21 |
| Ln(HF) | 5.05 ± 0.83 | 4.33 ± 1.09 | 2.31 ± 0.82 |
| LF/HF | 4.61 ± 2.33 | 2.77 ± 2.12 | 0.32 ± 0.20 |
| Ln(LF/HF) | 1.41 ± 0.51 | 0.75 ± 0.78 | −1.28 ± 0.52 |

*Mean slope of the log(power) versus log(frequency) between $10^{-4}$ and 10.2 Hz.

†Mean log(power) at $10^{-4}$ Hz computed from the power law regression equations, where power is measured in units of ms$^2$/Hz.

ULF, ultra low frequency; VLF, very low frequency; LF, low frequency; HF, high frequency. Ln denotes natural logarithm.

Values are mean ±SD.

The average value for log(power) at $10^{-4}$ Hz for healthy middle-aged subjects is 6.87±0.24 compared with 6.56±0.36 for the myocardial infarction group (t=15.82, p<0.0001) and compared with 6.56±0.29 for the heart transplant group (t=20.19, p<0.0001; units of power are ms$^2$/Hz). The average slope is −1.06±0.12 for middle-aged healthy subjects compared with −1.15±0.19 for the myocardial infarction group (t=8.99, p<0.0001) and compared with −2.08±0.22 for the heart transplant group (t=4.56, p<0.001). Thus both slope and log(power) at $10^{-4}$ Hz are significantly affected by myocardial infarction and the slope of the regression line is profoundly affected by disease or denervation of the heart. The increase in the steepness of the average slope in diseased or denervated hearts indicates that the fractional loss of power is substantially greater at higher frequencies.

FIGS. 3(a)–(f) show the frequency distributions for slope of log(power) on log(frequency) and the point log(power) at $10^{-4}$ Hz for the healthy group, the myocardial infarction group, and the transplant group. Compared to the healthy group, the distributions for both variables in patients with myocardial infarction are broader and extend further to the left, toward steeper slopes and lower values of log(power) at $10^{-4}$ Hz. However, there is substantial overlap between the distributions of slope and log(power) at $10^{-4}$ Hz for the healthy and myocardial infarction groups. Not only do transplant patients have considerably steeper slopes than either of the other groups, as seen in Table 1 and FIG. 2, but also there is no overlap in the slope values between the transplant group and the healthy group. The distribution of log(power) $10^{-4}$ Hz for the transplant group overlaps with that of the other groups.

Correlations Between Slope, Log(Power) at $10^{-4}$ Hz, and Log(Power) in Power Spectral Bands By convention, the 24-hour RR interval power spectrum has been divided into four bands by integrating under segments of the spectrum. Total power is obtained by integrating under the entire spectrum from about 0.00001 Hz to 0.04 Hz. Table 1 compares the new power law spectral measures of RR variability with previously published power spectral measures. Bigger, J. T. et al, "RR Variability in Healthy, Middle-Aged Persons Compared with Patients with Chronic Coronary Heart Disease of Recent Acute Myocardial Infarction," Circulation 91:1936–1943, 1995; Bigger et al., "Correlations Among Time and Frequency Domain Measures of Heart Period Variability Two Weeks After Myocardial Infarction," Am. J. Cardiol. 69:891–898, 1992; Bigger et al., "Correlations Among Time and Frequency Domain Measures of Heart Period Variability Two Weeks After Myocardial Infarction," Am. J. Cardiol. 69:891–898, 1992. No statistical tests are presented to evaluate differences between the healthy group and the diseased groups since this comparison has already been published. Bigger, J. T. et al., "RR Variability in Healthy, Middle-Aged Persons Compared with Patients with Chronic Coronary Heart Disease of Recent Acute Myocardial Infarction," Circulation 91:1936–1943, 1995. Table 2 shows the correlations between each power spectral band we have used for prediction of mortality in coronary heart disease and the slope of the log(power) versus log(frequency) relationship between $10^{-4}$ and $10^{-2}$ Hz, as well as the correlations between each power spectral band and the log(power) $10^{-4}$ Hz.

TABLE 2

Correlations Among Power Spectral Measures of RR Variability for Healthy Middle-Aged Subjects (n = 274), Patients with Recent Acute Myocardial Infarction (n = 715), and Heart Transplant Patients (n = 19)

| Power Measure | Slope* | | | Log(power) at $10^{-4}$ Hz† | | |
|---|---|---|---|---|---|---|
| | Healthy | Post Infarction | Transplant | Healthy | Post Infarction | Transplant |
| Log(power) at $10^{-4}$ Hz Power, ms$^2$ | −0.477 | −0.216 | −0.482 | 1.000 | 1.000 | 1.000 |
| Ln(Total) | 0.023 | 0.258 | 0.332 | 0.617 | 0.759 | 0.445 |
| Ln(ULF) | −0.037 | 0.176 | 0.314 | 0.598 | 0.759 | 0.459 |
| Ln(VLF) | 0.371 | 0.612 | 0.803 | 0.575 | 0.605 | 0.089 |
| Ln(LF) | 0.345 | 0.552 | 0.838 | 0.350 | 0.522 | −0.200 |

TABLE 2-continued

Correlations Among Power Spectral Measures of RR Variability for Healthy Middle-Aged Subjects (n = 274), Patients with Recent Acute Myocardial Infarction (n = 715), and Heart Transplant Patients (n = 19)

| Power Measure | Slope* | | | Log(power) at $10^{-4}$ Hz† | | |
|---|---|---|---|---|---|---|
| | Healthy | Post Infarction | Transplant | Healthy | Post Infarction | Transplant |
| Ln(HF) | 0.249 | 0.323 | 0.863 | 0.348 | 0.506 | −0.190 |
| Ln(LF/HF) | 0.052 | 0.410 | 0.600 | −0.103 | 0.109 | −0.169 |

*Slope of the log(power) versus log(frequency) between $10^{-4}$ and $10^{-2}$ Hz.
†Log(power) at $10^{-4}$ Hz computed from the power law regression equation, where power is measured in units of ms$^2$/Hz.
ULF, ultra low frequency power;
VLF, very low frequency power;
LF, low frequency power;
HF, high frequency power;
Ln denotes natural logarithm.
Power spectral values are logarithmically transformed to normalize their distributions.

The slope has only weak correlations with ln(total power) or ln(power) in any frequency band, but the largest correlations are with the middle bands in the spectrum, ln(VLF power) and ln(LF power). Log(power) at $10^{-4}$ Hz correlates best with ln(total power) and with ln(ULF power), the lowest frequency band under the 24-hour RR interval power spectrum. The correlations get progressively smaller with higher frequency bands.

Location of "Zero-Correlation Log(Power)"

Figure 4:
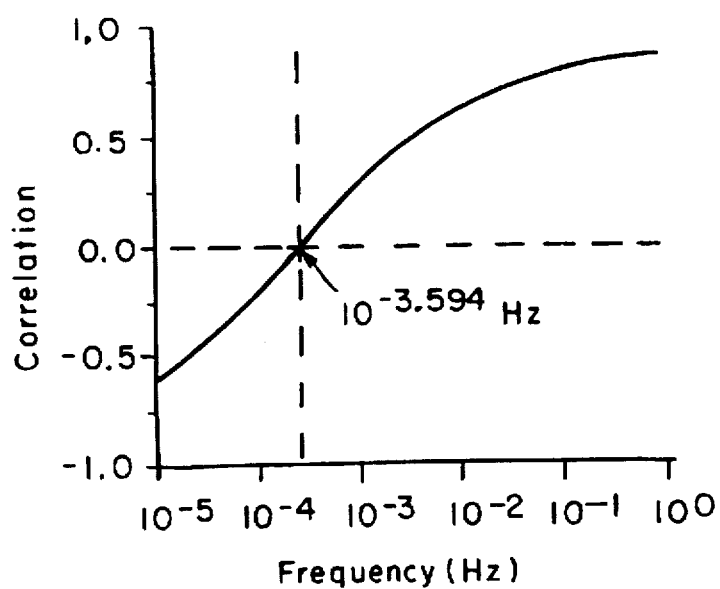
FIG. 4 is a graph showing correlation between slope and log(power) on the y-axis as a function of frequency on the x-axis, among the 715 power law regression equations of the myocardial infarction group. As frequency ranges from $10^{-5}$ Hz to 1 Hz, this function is S-shaped. For lower values on the abscissa, the computer power has a negative correlation with slope; for higher values, a positive correlation. At $10^{-3.594}$ Hz, the correlation equals zero.
Figure 3A:
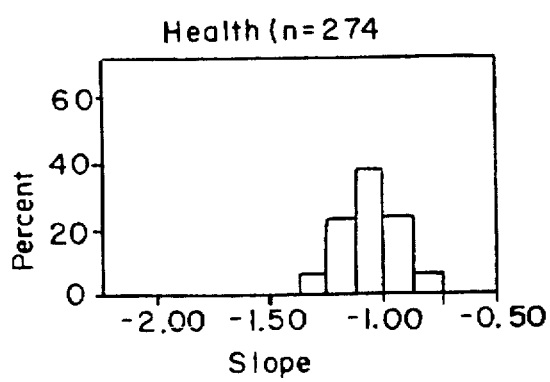
FIGS. 3($a$)–($f$) are graphs comparing frequency distributions of two power law regression parameters, slope (FIGS. 3($a$)–($c$)) and power at $10^{-4}$ Hz (FIGS. 3($d$)–($f$)) among three groups: healthy subjects (n=274), myocardial infarction patients (n=715), and heart transplant patients (n=19). Note that the distributions of both measures shown for myocardial infarction patients are wider, i.e., extend further to the left, than those for healthy subjects or heart transplant patients. In the heart transplant group, the distribution for slope values is narrow and shifts far to the left; there is little overlap with slope values for the myocardial infarction group and no overlap with slope values for the healthy group.
Figure 3D:
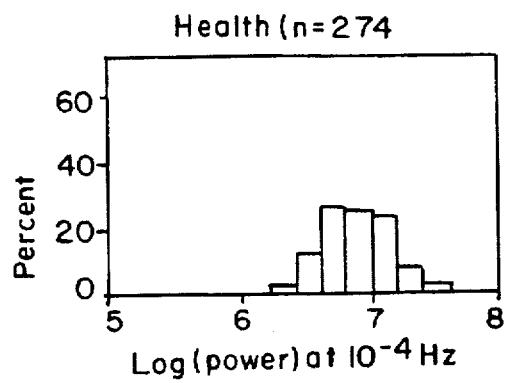
Figure 3B:
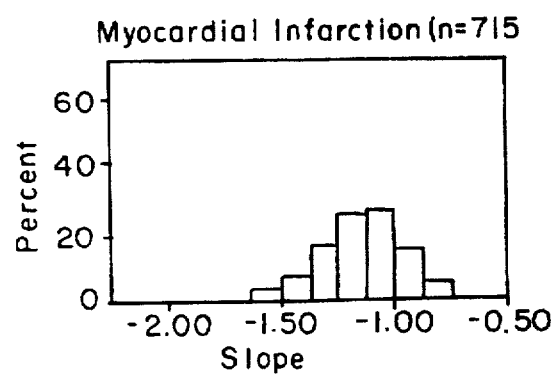
Figure 3E:
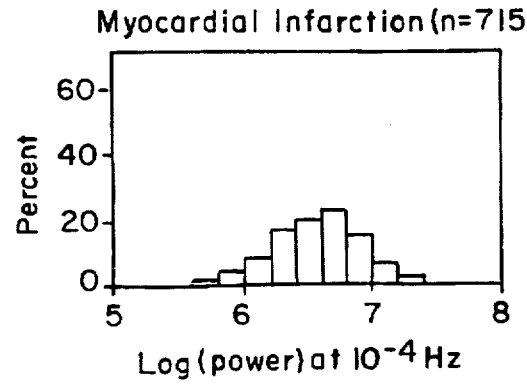
Figure 3C:
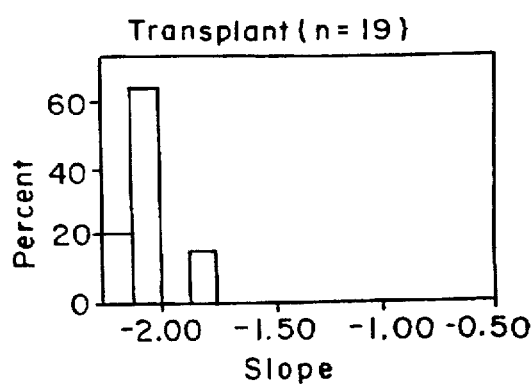
Figure 3F:
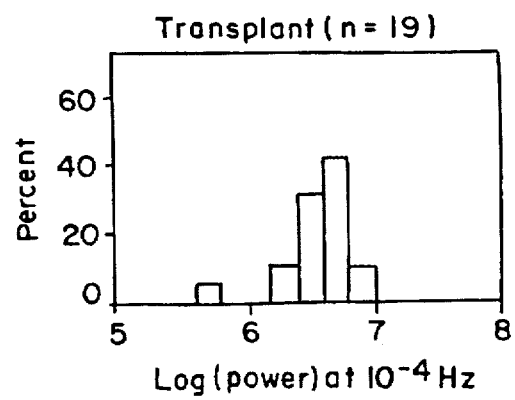

FIG. 4 shows the correlation between slope and log (power) as a function of frequency in the myocardial infarction group. We found that for lower values on the abscissa, e.g., $10^{-4}$ Hz, log(power) had a negative correlation with slope. In other words, patients with steeper (more negative) slopes tended to have higher power at lower frequencies. In contrast, we found that for higher values on the abscissa, e.g. $10^{-2}$ Hz power had a positive correlation with slope, i.e., patients with steeper slopes tended to have lower power at higher frequencies. Over the range $10^{-5}$ Hz to 1 Hz, the relationship is described by an S-shaped curve that passes through zero only once, i.e., $10^{-3.594}$ Hz, the frequency at which there is no correlation between log (power) and slope for the 715 patients in the myocardial infarction group.

Since there is no correlation between slope and the zero-correlation log(power), they should be multiplicative in predicting risk. Thus, it should be possible to estimate the mortality risk at 3 years for patients with high-risk values for both slope and zero correlation power by multiplying the relative risk of mortality for patients with high-risk values for slope, 2.92, by the relative risk for those with high-risk zero correlation values, 2.94. This procedure estimates a relative risk of 8.58, which is within the 95% confidence interval of the relative risk of 7.05, obtained directly from the Kaplan-Meier survival curves.

Risk Prediction Based on Slope and The Zero-Correlation Log(Power) used as Dichotomous Variables The best cutpoint for predicting risk after myocardial infarction with the slope of the power spectral regression line was −1.372; patients with steeper slopes, i.e., more negative values, were at greater risk. The best cutpoint for predicting death after myocardial infarction with the log (power) $10^{-4}$ Hz was 6.345. The best cutpoint for predicting death after myocardial infarction with zero-correlation log (power) (log(power) at $10^{-3.594}$ Hz) was 5.716. Power is measured in units of $ms^2/Hz$. Note that for zero-correlation log(power), the frequency at which it is computed is data-dependent. To be applied to a different population, this frequency, in addition to its cutpoint, would have to be computed with a representative sample of that population. Table 3 lists the variables slope, log(power) at $10^{-4}$ Hz, and zero-correlation log(power) at their optimum cutpoints, the numbers of patients in the groups categorized as having low or high values for the variable, and the Kaplan-Meier 3-year all-cause mortality rates for patients in the high and low categories for each variable.

Strength of association (relative risk) and statistical of significance of association are shown in Table 4.

Table 4 shows the significance (Z value) and strength of association (relative risk) obtained from the Cox regression analysis for the slope, the log(power) at $10^{-4}$ Hz and zero-correlation log(power), all dichotomized, and three mortality endpoints, all-cause, cardiac, and arrhythmic death.

TABLE 3

Cutpoints Used to Dichotomize Power Law Regression Parameters for Post-Infarction Mortality Analyses (n = 715)

| | | | Below Cutpoint | | At or Above Cutpoint | |
|---|---|---|---|---|---|---|
| Variable | Cutpoint | Percent Below Cutpoint | N | Kaplan-Meier 3 Year Mortality Rate | N | Kaplan-Meier 3 Year Mortality Rate |
| Slope* | −1.372 | 10.8% | 77 | 41.5% | 638 | 14.2% |
| Log(power) at $10^{-4}$ Hz† | 6.345 | 26.4% | 189 | 32.6% | 526 | 11.7% |
| Zero-correlation log(power)‡ | 5.716 | 11.9% | 102 | 40.0% | 613 | 13.4% |

*Slope of the log(power) versus log(frequency) between $10^{-4}$ and $10^{-2}$ Hz.
†Log(power) at $10^{-4}$ Hz is computed from the power law regression equation, where power is measured in units of $ms^2/Hz$.
‡Log(power) at $10^{-3.594}$ Hz computed from the power law regression equation, where power is measured in units of $ms^2/Hz$. For the Post Infarction sample, $10^{-3.594}$ Hz is the frequency at which there is no correlation between slope and log(power).

TABLE 4

Prediction of All-Cause Mortality After Myocardial Infarction by Power Spectral Measures of RR Variability Before and After Adjusting for Other Post Infarction Risk Predictors* Using Cox Regression Analysis (n = 715)

| | Mortality | | | | | | | | | | | |
|---|---|---|---|---|---|---|---|---|---|---|---|---|
| | All Cases (119 Deaths) | | | | Cardiac (88 Deaths) | | | | Arrhythmic (68 Deaths) | | | |
| | Unadjusted | | Adjusted | | Unadjusted | | Adjusted | | Unadjusted | | Adjusted | |
| Variable | Z† | Relative Risk‡ | Z† | Relative Risk‡ | Z† | Relative Risk‡ | Z† | Relative Risk‡ | Z† | Relative Risk‡ | Z† | Relative Risk |
| Slope§ | 5.61 | 3.40 | 2.57 | 1.86 | 5.42 | 3.83 | 2.79 | 2.11 | 5.35 | 4.42 | 3.02 | 2.51 |
| Log(power) at $10^{-4}$ Hz‖ | 6.37 | 3.29 | 3.55 | 2.05 | 5.49 | 3.30 | 2.68 | 1.89 | 4.60 | 3.15 | 2.21 | 1.82 |
| Zero-correlation log(power) | 6.49 | 3.66 | 3.28 | 2.08 | 5.95 | 3.95 | 2.82 | 2.07 | 4.57 | 3.45 | 2.03 | 1.86 |
| Power, $ms^2$ | | | | | | | | | | | | |
| Total | 6.79 | 4.14 | 3.16 | 2.12 | 5.47 | 3.90 | 2.36 | 1.91 | 4.62 | 3.79 | 2.08 | 1.95 |
| ULF | 7.33 | 4.76 | 3.94 | 2.58 | 6.21 | 4.76 | 3.45 | 2.60 | 5.31 | 4.71 | 3.07 | 2.69 |
| VLF | 6.63 | 3.77 | 2.31 | 1.70 | 6.11 | 4.11 | 2.04 | 1.72 | 5.64 | 4.41 | 2.28 | 2.00 |
| LF | 5.18 | 3.09 | 1.74 | 1.53 | 5.11 | 3.56 | 1.85 | 1.66 | 4.62 | 3.69 | 1.94 | 1.84 |
| HF | 3.42 | 2.23 | 1.62 | 1.50 | 3.56 | 2.59 | 1.94 | 1.72 | 2.84 | 2.39 | 1.70 | 1.72 |
| LF/HF | 4.67 | 2.69 | 2.05 | 1.60 | 3.51 | 2.42 | 1.30 | 1.42 | 3.35 | 2.61 | 1.44 | 1.56 |

*Adjusted for age, New York Heart Association functional class, rales, left ventricular ejection fraction and average frequency of ventricular premature complexes.
†$Z \leq 1.96$, $p < 0.05$; $Z \leq 2.58$, $p < 0.01$; $Z \leq 3.30$, $p < 0.001$
‡Relative risk is the probability of dying if below the cutpoint divided by the probability of dying if above the cutpoint.
§Slope of the log(power) versus log(frequency) between $10^{-4}$ and $10^{-2}$ Hz, dichotomized as shown in Table 3.
‖Log(power) at $10^{-4}$ Hz computed from the power law regression equation, where power is measured in units of $ms^2/Hz$, dichotomized as shown in Table 3.

Log(power) at $10^{-3.594}$ Hz computed from the power law regression equation, where power is measured in units of $ms^2/Hz$. For the post infarction sample, $10^{-3.594}$ Hz is the frequency at which there is no correlation between slope and power. This variable is dichotomized as shown in Table 3.

For comparison, the power spectral bands used for risk prediction after myocardial infarction also are tabulated. Each power spectral variable was evaluated individually in a Cox regression model. Table 4 also tabulates the significance (Z value) and strength of association (relative risk) after adjusting for the five risk predictor covariates that we have previously found to be strongly associated with mortality. The slope, the log(power) at $10^{-4}$ Hz, and zero-correlation log(power) all have associations with the three mortality endpoints that are comparable with the power in the spectral bands that have been used for risk prediction after myocardial infarction.

Table 5 shows the significance (Z value) and strength of association (relative risk) for the slope and each power measure, all dichotomized, with three mortality endpoints, all-cause, cardiac, and arrhythmic death when the slope and one of the two power measures are entered simultaneously into a Cox regression model.

was no statistically significant difference between the two relative risks (Z=0.86; NS). This indicates that log(power) at $10^{-4}$ Hz and slope provide predictive power similar to zero-correlation log(power) and slope.

Figure 5:
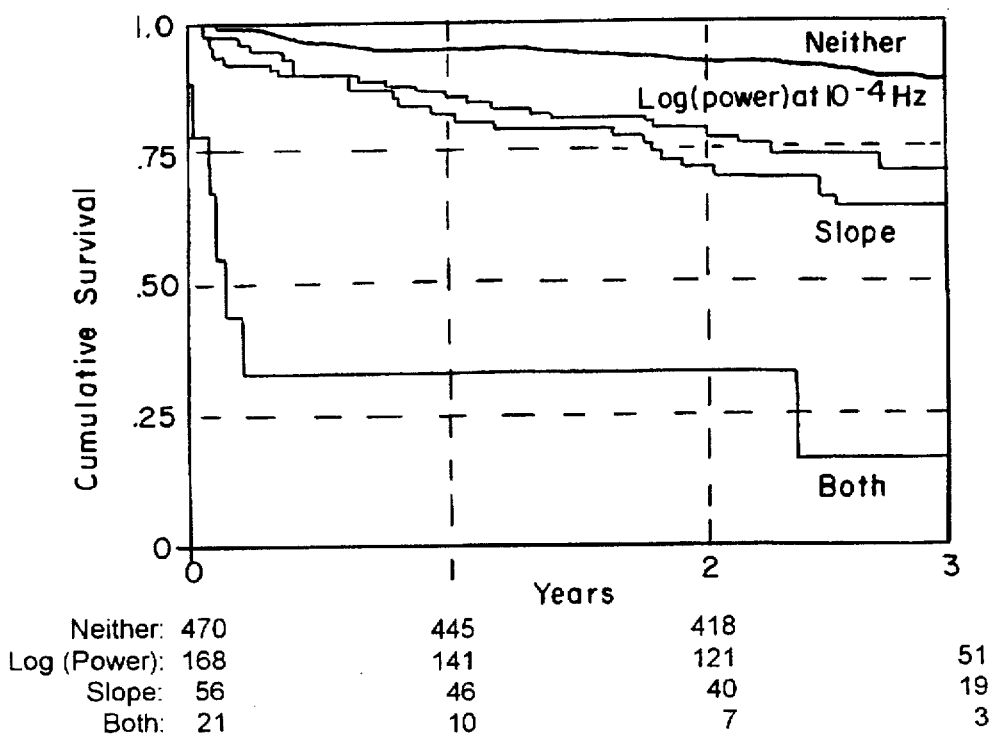
FIG. 5 includes Kaplan-Meier survival curves for 715 myocardial infarction patients cross-classified by optimum cutpoints for slope on the power law regression line (dichotomized at −1.372) and log(power) at $10^{-4}$ Hz (dichotomized at 6.345). The 3-year survival rates were: for patients in neither high-risk category, labelled "Neither," 89%; for patients in the high risk category for low (power) at $10^{-4}$ Hz only, labelled "Log(power) at $10^{-4}$ Hz," 70%; for patients in the high risk category for slope only, labelled "Slope," 64%; for patients in the high-risk category for both variables, labelled "Both," 17%;. The survival curve labelled "Log(power) at $10^{-4}$ Hz" is thinner than the other three curves, to distinguish it from the survival curve labelled "Slope." For each of the four groups, the numbers of patients being followed at enrollment and at 1, 2, and 3 years is shown below the graph.

To determine the joint predictive value of the two power law regression parameters (slope and log(power) at $10^{-4}$ Hz) for all-cause mortality, we cross-classified the MPIP sample using the two regression parameters and displayed the survival experience graphically using the Kaplan-Meier method (FIG. 5). Each patient was classified as high risk on neither, either, or by both slope and log(power) at $10^{-4}$ Hz. Fully 66% of the patients were classified as low risk on both parameters and only 21 (3%) patients were in the high risk category for both slope and log(power) at $10^{-4}$ Hz. The 3-year actuarial survival rates for the four groups were: low risk on both variables, 89%; high risk on slope, 64%; high risk on log(power) at $10^{-4}$ Hz, 70%; and high risk on both slope and log(power) at $10^{-4}$ Hz, 17%.

Figure 6:
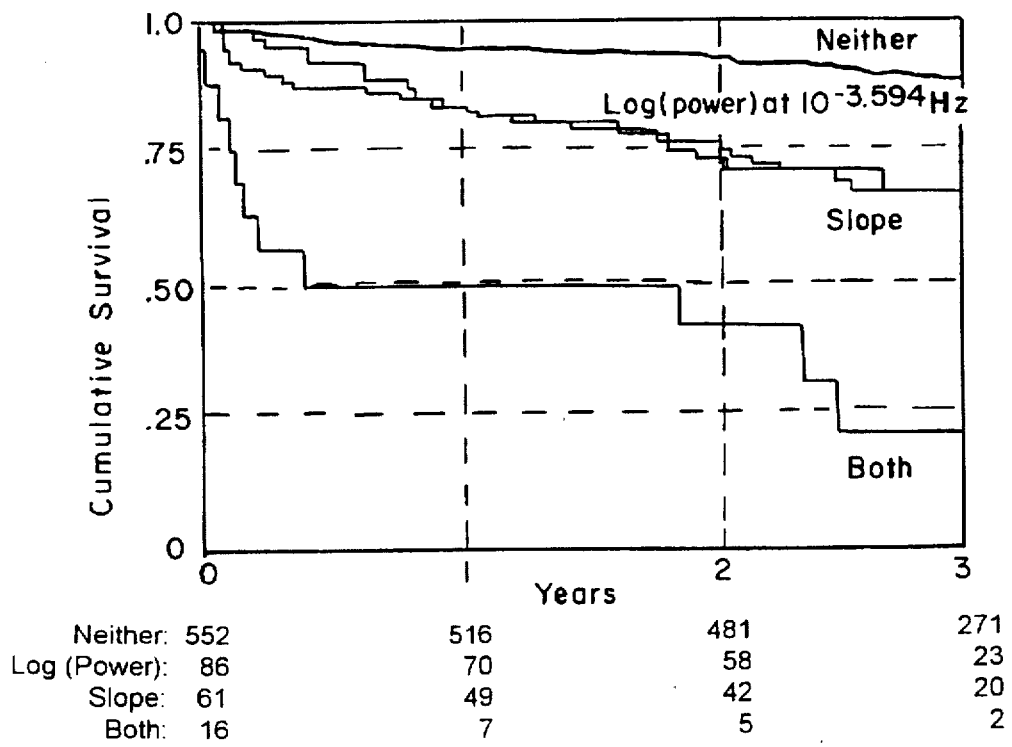
FIG. 6 includes Kaplan-Meier survival curves for 715 myocardial infarction patients cross-classified by optimum cutpoints for slope of the power law regression line (dichotomized at −1.372) and zero-correlation log(power) (dichotomized at 5.716). The 3-year survival rates were: for patients in neither high-risk category, labelled "Neither," 89%; for patients in the high risk category for zero-correlation log(power) only, labelled "Log(power) at $10^{-3.594}$ Hz," 67%; for patients in the high risk category for slope only, labelled "Slope," 67%; for patients in the high-risk category for both variables, labelled "Both," 21%;. The survival curve labelled "Log(power) at $10^{-3.594}$ Hz" is thinner than the other three curves, to distinguish it from the survival curve labelled "Slope." For each of the four groups, the numbers of patients being followed at enrollment and at 1, 2, and 3 years is shown below the graph.

FIG. 6 shows similar Kaplan-Meier curves for the four subgroups cross-classified by slope and the zero-correlation log(power). There were 102 (14%) with a zero-correlation log(power) less than 5.716 $log(ms^2/Hz)$. Sixteen (2%) patients were in the high risk category for both slope and

TABLE 5

Prediction of All-Cause Mortality After Myocardial Infarction with Power Law Regression Parameters Using Cox RegressionModels with and Without Adjusting for Other Post Infarction Risk Predictors* (n = 715) Two Models are Shown: the First Includes both Slope and the Log(Power) at $10^{-4}$ Hz; the Second Model Includes both Slope and the Zero-Correlation Log(Power)

| | Mortality | | | | | | | | | |
|---|---|---|---|---|---|---|---|---|---|---|
| | All Cases (119 Deaths) | | | | Cardiac (88 Deaths) | | | | Arrhythmic (68 Deaths) | |
| | Unadjusted | | Adjusted | | Unadjusted | | Adjusted | | Unadjusted | Adjusted |
| Variable | Z† | Relative Risk‡ | Z† | Relative Risk‡ | Z† | Relative Risk‡ | Z† | Relative Risk‡ | Z† | Relative Risk‡ | Z† | Relative Risk |
| Slope§ | 6.28 | 4.01 | 3.49 | 2.37 | 5.93 | 4.43 | 3.60 | 2.70 | 5.72 | 4.98 | 3.72 | 3.21 |
| Log(power) $10^{-4}$ Hz‖ | 6.86 | 3.64 | 4.20 | 2.39 | 5.90 | 3.65 | 3.44 | 2.31 | 4.95 | 3.46 | 3.01 | 2.33 |
| Slope§ | 5.75 | 3.51 | 3.00 | 2.07 | 5.44 | 3.86 | 3.20 | 2.37 | 5.32 | 4.39 | 3.32 | 2.75 |
| Zero-correlation log(power) | 6.61 | 3.75 | 3.63 | 2.25 | 5.97 | 3.97 | 3.22 | 2.30 | 4.53 | 3.43 | 2.44 | 2.11 |

*Adjusted for age, New York Heart Association functional class, rales, left ventricular ejection fraction and average frequency of ventricular premature complexes.
†Z ≦ 1.96, p < 0.05; Z ≦ 2.58, p < 0.01; Z ≦ 3.30, p < 0.001
‡Relative risk is the probability of dying if below the cutpoint divided by the probability of dying if above the cutpoint.
§Slope of the log(power) versus log(frequency) between $10^{-4}$ and $10^{-2}$ Hz, dichotomized as shown in Table 3.
‖Log(power) at $10^{-4}$ Hz computed from the power law regression equation, where power is measured in units of $ms^2/Hz$, dichotomized as shown in Table 3.

Log(power) at $10^{-3.594}$ Hz computed from the power law regression equation, where power is measured in units of $ms^2/Hz$, dichotomized as shown in Table 3. For the post infarction sample, $10^{-3.594}$ Hz is the frequency at which there is no correlation between slope and power.

The strength and significance of the slope and a power measure in the multivariate model are similar to those found in the univariate models, reflecting a low correlation between these variables. Patients in the higher risk category for the slope and a power measure are at very high risk. For example, the relative risk for all-cause mortality is 14.40 (4.01×3.64) for patients who are categorized as high risk by both slope and the log(power) at $10^{-4}$ Hz.

When we used the jackknife technique to compare the relative risk for patients with high risk values for both the slope and the log(power) at $10^{-4}$ Hz to the relative risk obtained for patients with high risk values for both the slope and the zero-correlation log(power), it was found that there zero-correlation log(power). The 3-year actuarial survival for the four groups were: low risk on both variables, 89%; high risk on slope, 67%; high risk on zero-correlation log(power), 67%; and high risk on both slope and zero-correlation log(power), 21%.

Risk Prediction Based on Joint Variables from Power Law Regression Analysis

The slope and zero-correlation log(power) were used as components of joint predictor variables in Cox regression analyses, as were the slope and log(power) at $10^{-4}$ Hz. In these analyses, patients classified as high risk by slope and the log(power) at $10^{-4}$ Hz had a relative risk of 10.16 (p<0.001); patients classified as high risk by slope and the zero-correlation log(power) had a relative risk of 11.23 (p<0.001). When the joint variable comprised of slope and the log(power) at $10^{-4}$ Hz was adjusted for age, New York Heart Association functional class, left ventricular ejection fraction, and average frequency of ventricular premature complexes, the relative risk was 6.07 (p<0.001). When the joint variable comprised of slope and the zero-correlation log(power) was so adjusted, the relative risk was 5.57 (p<0.001).

When ULF and VLF were similarly combined into a variable indicating high-risk classification for both ULF and VLF, the resulting variable had a relative risk of 4.85 (p<0.001). When adjusted in the same manner as the joint variables comprised of the 2 power law measures, the relative risk was 2.98 (p<0.001). This was considerably lower than the relative risk for the joint variables comprised of the 2 power law measures.

The purpose of this study was to quantify the power law aspect of the 24-hour RR interval time series in healthy subjects, in denervated (transplanted) hearts, and in patients with recent myocardial infarction, and to determine the ability of power law regression parameters to predict death after myocardial infarction. From preliminary studies, the spectral power of RR interval fluctuations seemed to be an inverse, linear function of frequency from somewhat above $10^{-2}$ Hz to below $10^{-4}$ Hz in a log—log graph. Based on these preliminary observations, we decided to fit a linear regression to log(power) as a function of log(frequency) between $10^{-4}$ and $10^{-2}$ Hz. We found that this relation in fact was linear, i.e., the goodness of fit was excellent in healthy subjects, in patients with denervated hearts, and in patients with recent myocardial infarction.

The slope computed over the two-decade band $10^{-4}$ to $10^{-2}$ Hz is a fundamentally different RR interval power spectral measure than the standard band power components ULF, VLF, LF, or HF. In contrast to these, the slope reflects not the magnitude but rather the distribution of power in this two-decade region. The average slope was close to $-1$ for the healthy middle-aged subjects in our study. A slope of exactly $-1$ on a log—log graph (where $\alpha$ in equation [1] is equal to $-1$) means that spectral power is proportional to the reciprocal of frequency. In other words, there is a unit decrease in power for every unit increase in frequency. A slope of $-1$ also means that power in the lower decade, $10^{-4}$ to $10^{-3}$ Hz, is equal to power in the higher decade, $10^{-3}$ to $10^{-2}$ Hz. But since the width of the lower decade is one-tenth that of the higher, the spectral density in the lower decade, expressed as power per unit frequency (in this case $ms^2/Hz$), is ten times that of the higher decade. The steeper the slope, the greater the power in the lower frequency ranges relative to the higher frequency ranges.

These frequency-domain features—linearity and slope near—1—have implications in the time domain. First, the variance of relatively rapid RR interval oscillations with periods from 100 seconds to 1000 seconds (i.e., approximately 2 to 20 minutes, corresponding to $10^{-2}$ to $10^{-3}$ Hz) will equal the variance of much slower oscillations with periods from 1000 to 10,000 seconds (i.e., up to about 3 hours, corresponding to $10^{-4}$ Hz). Thus, plots of RR interval versus time over 2 minutes, 20 minutes, and 3 hours may appear similar. This feature, called scale invariance or self-similarity, distinguishes a broad-band frequency spectrum, wherein no single frequency component characterizes a signal, from a narrow-band spectrum as might be found, for example, in the HF power band of the RR interval power spectrum during metronome breathing. Fractal mathematics, well-suited to describe such scale-invariance signals, has already been applied in an exploratory fashion to RR interval time series analysis, see, Goldberger et al., "Fractals in Physiology and Medicine," *Yale J. Biol. Med.* 60:421–435, 1987, and might be used for risk-stratification in larger data sets.

Because power is an inverse function of frequency, RR interval variance is a direct function of time, i.e., variance increases with the length of observation, another feature of a broad-band spectrum. In contract, the variance of a signal with a narrow-band spectrum, such as a sine wave, closely approaches a constant value after the length of observation encompasses a few cycles. Therefore, RR interval variance, or its square root, SDNN, is meaningful only with respect to a particular duration of electrocardiographic recording. This is true whether the slope of the log-transformed power spectrum is $-1$ as in the healthy sample or $-2$ as in the denervated heart (patients with heart transplants). One implication of the power law relation between spectral power of RR interval fluctuations and their frequency is the need to correct SDNN for differences in the duration of Holter ECG recordings.

Effect of Myocardial Infarction and Cardiac Transplantation on Power Spectral Regression Parameters.

In normal middle-aged subjects, the slope of the log (power) on log(frequency) regression line is very close to $-1$. Myocardial infarction and cardiac transplantation (denervation) shift the entire regression line down, i.e., power spectral density is decreased at any frequency (FIGS. 3(a)–(f)). The average slope of the regression line is much steeper (about $-2$) for patients with heart transplants (denervated) than for age- and sex-matched healthy subjects (average slope about $-1$). Thus, the range of the slope is 1 when comparing healthy, innervated hearts to transplanted, denervated hearts. The average slope of the regression line for patients with myocardial infarction is closer to values for healthy subjects (about $-1.15$) than to values for transplanted, denervated hearts. However, after myocardial infarction, the values for the slope vary from normal at one extreme of the distribution to values that approach those of the transplanted, denervated hearts at the other end of the distribution. The change in the slope when the heart is denervated by transplantation suggests that the slope is substantially influenced by the heart's autonomic inputs.

The Correlation between Power Spectral Regression Parameters and Other Power Spectral Measures of RR Variability.

Figure 7:
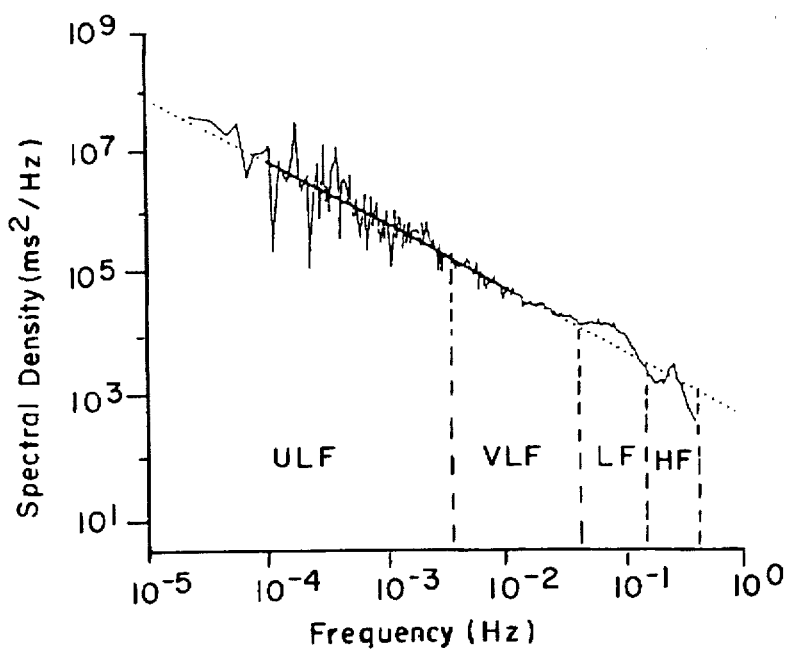
FIG. 7 is a graph illustrating the relationship between regression of power spectral density for RR interval fluctuations on frequency and traditional spectral bands for a healthy subject. The computed power law regression line is superimposed on the data; the darkened portion of the lines is the segment between $10^{-4}$ and $10^{-2}$ Hz. ULF, ultra low frequency; VLF, very low frequency; HF, high frequency. In the region of the ULF and VLF bands, the log—log graph of spectral power versus frequency is linear. In the region of the LF and the HF bands, the log—log graph of spectral power versus frequency is non-linear due to modulation by the autonomic nervous system.

FIG. 7 diagrams the relationship between the power law regression line and traditional power spectral bands for a healthy subject. Table 2 shows that there is very little correlation between any of the four power spectral bands and the slope of log(power) on log(frequency). There is a greater but still moderate correlation between log(power) at $10^{-4}$ Hz and the power spectral bands. Because the two power law regression parameters, slope and log(power) at $10^{-4}$ Hz, correlate only moderately with traditional power spectral bands (Table 2), the two regression parameters have the potential to predict risk better than the power spectral bands.

Slope and Intercept as Risk Predictors after Myocardial Infarction.

As shown in Table 4, slope and log(power) are significant and independent predictors of all-cause mortality, when adjusted for five post infarction risk predictors which we have previously found to be strongly associated with mortality.

Association Between Power Law Regression Parameters and Mortality.

In a previous study, we examined the association between mortality and four bands of the RR interval power spectrum as well as total power and LF/HF ratio (11). An analysis of the relationship between log(power) and log(frequency) produces two variables which reflect not only the magnitude but the frequency-dependence of the power spectral curve in the range $10^{-4}$ Hz to $10^{-2}$ Hz, frequencies corresponding to cycles of 2.7 hour and 1.7 minutes, respectively. This frequency range includes parts of the ultra low and the very low frequency bands, which were found to have a strong association with mortality.

Slope and log(power) are not independent, but are negatively correlated for lower values on the abscissa and positively correlated for higher values on the abscissa (FIG. 4). By calculating the zero-correlation log(power), we obtained two statistically independent variables, thereby maximizing the information obtained about the slope and amplitude of the power spectral curve. We did similar analyses using log(power) at $10^{-4}$ Hz instead of zero-correlation log(power). When used individually, the predictive value of slope and power measures were close to the predictive value of ultra low frequency or very low frequency power. When combined into joint variables indicating high risk classification for slope and zero-correlation log(power), or for slope and log(power) at $10^{-4}$ Hz, the relative risks of these joint variables were very high, i.e., >10. The relative risks were still high, >5 after these joint variables were adjusted for age, New York Heart Association functional class, left ventricular ejection fraction, and average frequency of ventricular premature complexes.

When ULF and VLF were similarly combined into a variable indicating high-risk classification for both ULF and VLF, the joint variable had a relative risk <5. When the ULF-VLF joint variable was adjusted for other post infarction risk predictors, the relative risk was <3. Thus, the ULF and VLF bands, the strongest predictors of the power spectral bands tested, have much lower joint predictive power than the joint variables comprised of the 2 power law measures. This is because of the strong correlation between the logarithmically transformed variables ULF and VLF, which is 0.75, as contrasted with the lack of correlation between the slope and zero-correlation log(power), and the considerably lower correlation of 0.48 between the slope and log(power) at $10^{-4}$ Hz. For this reason, the information provided by ULF and VLF is substantially redundant and, as a result, there is less gain in predictive value when they are combined.

Apparatus

Figure 8:
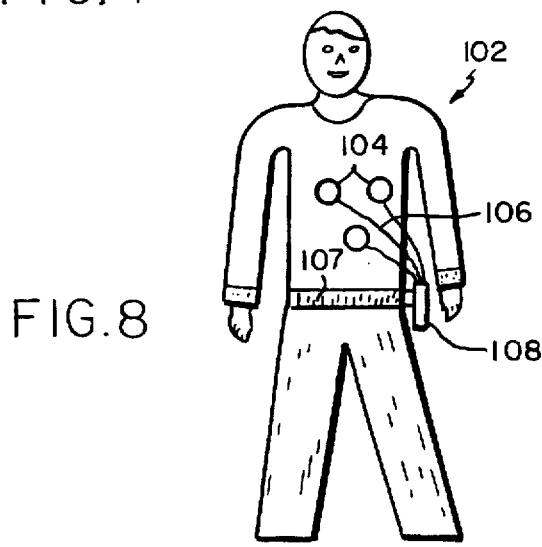
FIG. 8 is a schematic illustration of a human subject instrumented with electrodes for recording electrocardiographic activity and a portable recording apparatus.
Figure 9:
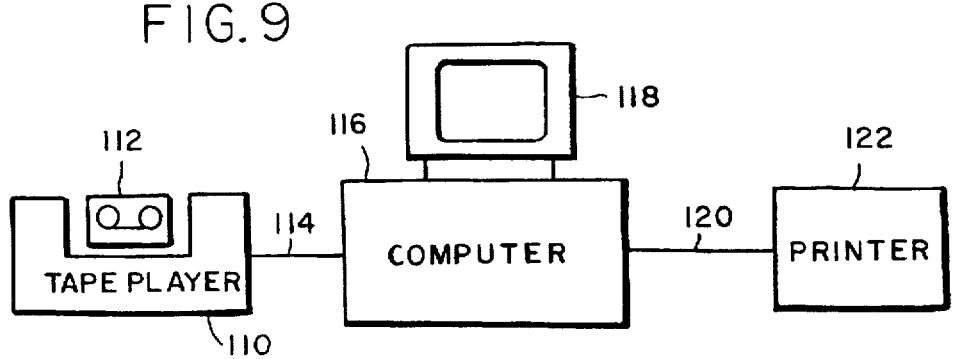
FIG. 9 is a schematic illustration of the apparatus for carrying out the present invention.
Figure 10A:
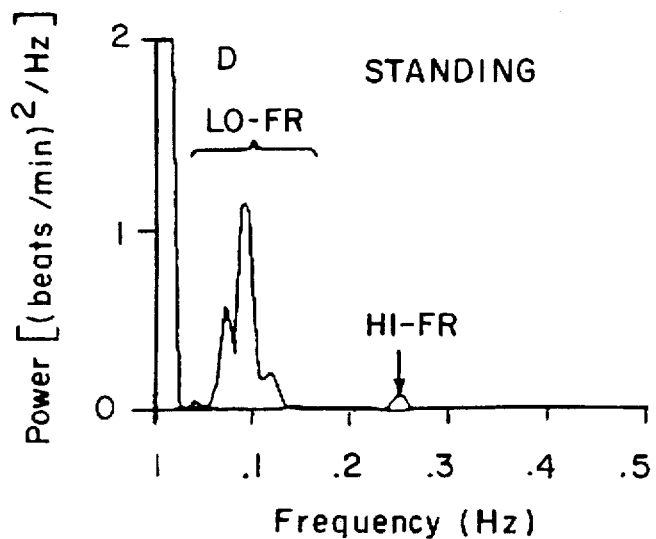
FIG. 10a is a graph of a heart rate power spectrum obtained on a standing human subject from a short, 256 second, data segment. This spectrum which approximately covers a 0.01–0.5 Hertz frequency range demonstrates the presence of the low frequency (LO-FR) and high-frequency (HI-FR) peaks. This figure is taken from Pomeranz B., Macaulay J. B., Caudill M. A., Kutz I, Adam D, Gordon D., Kilborn K. M., Barger A. C., Shannon D. C., Cohen R. J., Benson H. American Journal of Physiology 1988;248, H151–H153.
Figure 10B:
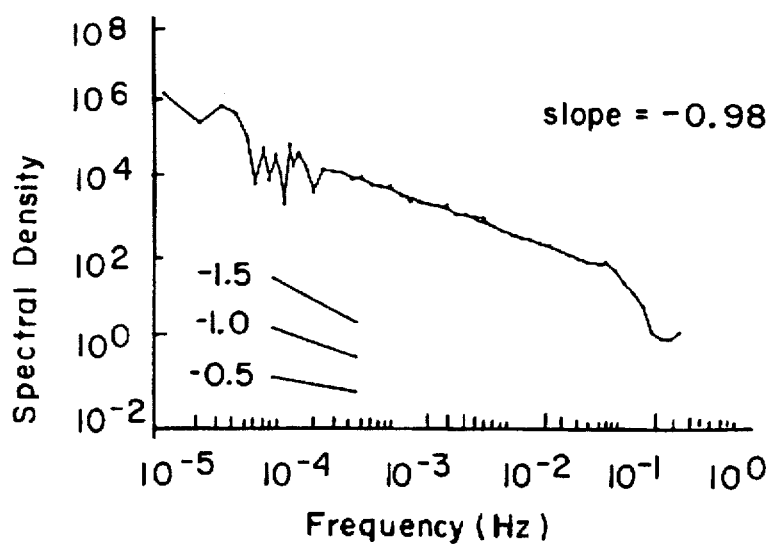
FIG. 10b is a graph of a heart rate power spectrum computed from interbeat interval data taken from a 24 hour ECG recording of a human subject. The graph shows the linear relationship between spectral density and frequency when plotted on a log—log plot over at least three decades of frequency above $10^{-5}$ Hertz. This figure is taken from Saul J. P., Albrecht P, Berger R. D. and Cohen R. J., Computers in Cardiology Conference Proceedings in Leuven Belgium, Sep. 12–15, 1987, Computer Society Press, Washington, Los Alamitos, Brussels.

The apparatus for carrying out the present invention will now be described in conjunction with FIGS. 8 and 9. A human subject 102 has had electrodes 104 applied for recording electrocardiographic activity. Wires 106 bring the electrocardiographic signals to portable recording apparatus 108. A belt 107 is used to hold the portable recording apparatus 108 on the subject 102. The portable recording apparatus 108 amplifies the electrocardiographic signals from the electrodes 104 and records them on magnetic tape. It is contemplated that the subject 102 will wear the portable recording apparatus 108 for an extended period of time such as for twelve to twenty-four hours.

After recording from the subject 102, a tape player 110 is used to play magnetic tape 112 on which the electrocardiographic signals have been recorded by the portable recording apparatus 108. Signals from the tape playback unit 110 are carried by cable 114 to a general purpose computer 116. The computer 116 also contains an analog-to-digital conversion board which converts analog electrocardiographic signals to digital form for analysis. The computer 116 processes the electrocardiographic signals recorded on the magnetic tape 112. In particular, the computer 116 is adapted to detect R waves of the electrocardiogram, compute interbeat intervals, and perform the analyses of the long-time structure of the fluctuations in the intervals discussed above in this specification. A video monitor 118 may be provided to display the results of the analyses performed by the computer 116. Similarly, the computer 116 may be connected to a printer 122 via a printer cable 120 so that the results of the computer analyses may be recorded on paper. The output of the computer 116 provides an assessment of risk of an adverse clinical event as discussed in detail throughout this specification.

It is recognized that modifications and variations of the present invention will occur to those skilled in the art and it is intended that all such modifications and variations be included within the scope of the appended claims.

What is claimed is:

1. Method for assessing risk of an adverse clinical event comprising:

detecting a physiologic signal in a subject;

determining from the physiologic signal a sequence of intervals corresponding to time intervals between heart beats; and analyzing long-time structure of fluctuation in the intervals to assess risk of an adverse clinical event.

2. The method of claim 1 wherein the physiologic signal is an electrocardiogram.

3. The method of claim 2 wherein the interval is the RR interval.

4. The method of claim 1 wherein the sequence of intervals spans a time period of at least fifteen minutes.

5. The method of claim 1 wherein the analyzing step involves computing the power spectrum of the fluctuation in the intervals.

6. The method of claim 5 wherein the amplitude of the power spectrum, at a specified frequency, is estimated, the amplitude of the power spectrum at the specified frequency being related to the risk of an adverse clinical event.

7. The method of claim 6 wherein the specified frequency is approximately $10^{-4}$ Hz.

8. The method of claim 6 further including the step of comparing the amplitude of the power spectrum with a predetermined risk-related cutpoint amplitude.

9. The method of claim 5 further involving fitting the power spectrum to a power law dependence on frequency, over a selected frequency range.

10. The method of claim 9 wherein the frequency range is approximately $10^{-4}$ to $10^{-2}$ Hz.

11. The method of claim 9 in which the amplitude of the power law dependence is determined at a specified frequency.

12. The method of claim 9 further including the step of comparing the amplitude of the power law dependence with a predetermined risk-related cutpoint amplitude.

13. The method of claim 11 wherein the specified frequency is approximately $10^{-4}$ Hz.

14. The method of claim 9 wherein an exponent characterizing the power law dependence is compared with a predetermined risk-related cutpoint exponent.

15. The method of claim 5 further involving fitting the logarithm of the power spectrum to a linear dependence on the logarithm of frequency, over a selected frequency range.

16. The method of claim 15 wherein the frequency range is approximately $10^{-4}$ to $10^{-2}$ Hz.

17. The method of claim 15 in which amplitude of the linear dependence is determined at a specified frequency.

18. The method of claim 17 further including the step of comparing the amplitude of the linear dependence with a predetermined risk-related cutpoint amplitude.

19. The method of claim 17 wherein the specified frequency is approximately $10^{-4}$ Hz.

20. The method of claim 15 wherein slope characterizing the linear dependence is compared with a predetermined risk-related cut-point slope.

21. The method of claim 15 applied to a reference population further including determining a frequency within the selected frequency range at which amplitude of the linear dependence has a low correlation with slope of the linear dependence.

22. The method of claim 1 wherein the physiologic signal is detected while the subject is ambulating.

23. The method of claim 1 wherein the physiologic signal is detected while the subject is engaged in an activity protocol.

24. Method for assessing risk of an adverse clinical event comprising:

detecting an electrocardiogram signal in a subject;

determining from the electrocardiogram a sequence of intervals corresponding to time intervals between heart beats;

computing the power spectrum of the sequence of intervals over a time period of more than 6 hours;

fitting the logarithm of the power spectrum to a linear dependence on the logarithm of frequency over the frequency range of approximately $10^{-4}$ to $10^{-2}$ Hz.; and assessing risk based on one or more characteristics of the linear dependence.

25. The method of claim 24 wherein one of the characteristics includes slope of the linear dependence.

26. In the method of claim 25 wherein one of the characteristics includes amplitude of the linear dependence at a specified frequency.

27. Apparatus for assessing risk of an adverse clinical event comprising:

electrodes responsive to physiologic signals in a subject to generate output signals;

electronic apparatus for receiving the output signals and for analyzing long-time structure of fluctuations in intervals between heartbeats over a time period of more than 15 minutes to assess risk of an adverse clinical event.

28. Apparatus for assessing risk of an adverse clinical event comprising:

recording apparatus adapted to record a physiologic signal in a subject; and electronic apparatus for analyzing the physiologic signal to determine long-time structure of fluctuations in intervals between heartbeats, the electronic apparatus further adapted for assessing risk of an adverse clinical event.

29. Apparatus for assessing risk of an adverse clinical event comprising:

apparatus for detecting a physiologic signal in a subject;

means for determining from the physiologic signal a sequence of intervals corresponding to time intervals between heartbeats; and electronic apparatus for analyzing long-time structure of fluctuations in the intervals to assess risk of an adverse clinical event.

30. The apparatus of claim 27, 28 or 29 wherein the time period is at least one hour.

31. The apparatus of claim 27, 28 or 29 wherein the analyzing involves computing the power spectrum of fluctuations in the intervals.

32. The apparatus of claim 31 further involving fitting the power spectrum to a power law dependence on frequency over a selected frequency range.

33. The apparatus of claim 32 wherein the selected frequency range is approximately $10^{-4}$ to $10^{-2}$ Hz.

34. Method for assessing risk of an adverse clinical event comprising analyzing long-time structure of fluctuations in intervals between heartbeats and assessing risk of an adverse clinical event based on an analysis of the long-time structure of fluctuations in the intervals.

35. The method of claim 34 further involving obtaining at least two measures of the fluctuations.

36. The method of claim 34 further comprising the step of computing serial auto-correlation coefficients of the fluctuations in intervals between heartbeats.

37. The method of claim 34 further involving the computation of a power spectrum of the fluctuations in intervals between heartbeats.

38. The method of claim 34 further involving a frequency analysis of the intervals between heartbeats.

39. The method of claim 34 further involving the computation of the magnitude of the fluctutations in at least two frequency bands, at least one of which includes a region below 0.02 Hz.

40. The method of claim 34 further involving the computation of the magnitude of fluctuations at, at least, two frequencies, at least one of which is below 0.02 Hz.

41. The method of claim 34 further involving autoregressive analysis of fluctuations in intervals between heartbeats.

42. The method of claim 34 further involving analysis of the fluctuations over at least two different length segments of an interbeat interval sequence.

43. The method of claim 42 wherein the analysis involves computation of the standard deviation or variance of intervals in the segments.

44. The method of claim 43 wherein the analysis involves computation of the average of NN intervals in the segments.

45. The method of claim 1 wherein the physiologic signal is detected while the subject is resting.

46. The method of claim 42 wherein the analysis involves analyzing the variability of the intervals within segments of a sequence of interbeat intervals.

47. The method of claim 42 wherein the analysis involves analyzing the variability between segments containing interbeat intervals of a measure of the intervals within segments.

48. A method for assessing risk of an adverse clinical event comprising analyzing the long term frequency dependence of fluctuations in intervals between heartbeats including at least two frequencies, one of which is below 0.02 Hz, the frequency dependence being related to risk of an adverse clinical event.

49. The method of claim 34 further involving the computation of an auto-correlation function of the fluctuations in intervals between heartbeats.

50. The method of claim 34 further involving Fourier analysis of fluctuations in intervals between heartbeats.

51. The method of claim 34 further involving wavelet analysis of fluctuations in intervals between heartbeats.

52. The method of claim 34 further involving polynomial analysis of fluctuations in intervals between heartbeats.

53. The method of claim 34 further involving Hankel analysis of fluctuations in intervals between heartbeats.

54. The method of claim 34 further involving complex demodulation analysis of fluctuations in intervals between heartbeats.

55. A method for assessing risk of an adverse clinical event comprising analyzing the variability in intervals between heartbeats utilizing segments of interbeat intervals of at least two different lengths; and assessing risk from the variability in intervals.

56. The method of claim 55 wherein the analysis involves analyzing the variability between segments of interbeat intervals of a measure of the intervals within segments.

* * * * *

UNITED STATES PATENT AND TRADEMARK OFFICE
CERTIFICATE OF CORRECTION

| | | |
|---|---|---|
| PATENT NO. | : 5,755,671 | Page 1 of 1 |
| APPLICATION NO. | : 08/539402 | |
| DATED | : May 26, 1998 | |
| INVENTOR(S) | : Paul Albrecht | |

It is certified that error appears in the above-identified patent and that said Letters Patent is hereby corrected as shown below:

Delete the paragraph encompassing column 1, lines 4-7:

"The Government has rights in this invention pursuant to National Institutes of Health (NIH) grant HL-39291 from the National Heart, Lung, and Blood Institute, Bethesda, Md. and by NASA Grant NAGW-3927."

and replace with:

--This invention was made with government support under Grant No. R01 HL039291 awarded by the National Institutes of Health and under Grant No. NAGW-3927 awarded by NASA. The government has certain rights in this invention.--

Signed and Sealed this
Thirtieth Day of October, 2012

David J. Kappos
*Director of the United States Patent and Trademark Office*